United States Patent
Yamamoto et al.

(10) Patent No.: US 6,255,094 B1
(45) Date of Patent: Jul. 3, 2001

(54) β-GALACTOSIDE-α2, 6-SIALYLTRANSFERASE GENE

(75) Inventors: Takeshi Yamamoto; Motoko Nakashizuka, both of Kanagawa-ken; Ichiro Terada, Osaka, all of (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 09/171,878

(22) PCT Filed: Mar. 2, 1998

(86) PCT No.: PCT/JP98/00850

§ 371 Date: Jan. 5, 1999

§ 102(e) Date: Jan. 5, 1999

(87) PCT Pub. No.: WO98/38315

PCT Pub. Date: Mar. 9, 1998

(30) Foreign Application Priority Data

Feb. 28, 1997 (JP) .................................................... 9-045087

(51) Int. Cl.$^7$ .............................. C12N 9/10; C07H 21/04
(52) U.S. Cl. ...................... 435/193; 435/69.1; 435/320.1; 530/300; 530/326; 536/23.1; 536/23.2
(58) Field of Search .................................... 435/193, 69.1, 435/320.1; 536/23.1, 23.2; 530/300, 326

(56) References Cited

FOREIGN PATENT DOCUMENTS

| 8154673A | 6/1996 | (JP) . |
| 173182 | 7/1996 | (JP) . |

OTHER PUBLICATIONS

Paulson et al., *The Journal of Biological Chemistry*, vol. 252, No. 7, Issue of Apr. 10, pp. 2356–2362 (1977).
Weinstein et al., *The Journal of Biological Chemistry*, vol. 257, No. 22, Issue of Nov. 25, pp. 13835–13844 (1982).
Miyagi et al., *Eur. J. Biochem.*, vol. 126, pp. 253–261 (1982).
Weinstein et al. Primary Structure of b–Galactoside a2,6–Sialyltransferase, J. Biol. Chem. 262(36): 17735–17743.*
T. Yamamoto et al., Journal of Biochemistry (Tokyo), vol. 1200, (1996).
T. Yamamoto et al., Journal of Biochemistry (Tokyo), vol. 123, (1998).

* cited by examiner

*Primary Examiner*—Rebecca E. Prouty
*Assistant Examiner*—Richard Hutson
(74) *Attorney, Agent, or Firm*—Birch, Stewart, Kolasch & Birch, LLP

(57) ABSTRACT

This invention provides to a novel gene encoding a protein aving the activity of β-galactoside-α2,6-sialyltransferase.

The gene of the invention encodes a protein which having the amino acid sequence of SEQ ID NO:1, or a protein having the amino acid sequence of SEQ ID NO:1 which have been modified by deletion, substitution or addition of at least one amino acid residue in said sequence, while maintaining substantially the same β-galactoside-α2,6-sialyltransferase activity.

The present invention uses said gene to further provide a vector for expressing a protein having the β-galactoside-α2, 6-sialyltransferase activity, host cells and a recombinant protein. The protein encoded by the gene of the invention does not have any substantial homology with known sialyltransferases, and in addition, the membrane binding region is located in the C-terminal unlike known sialyltransferases.

16 Claims, 10 Drawing Sheets

Expresion vector, pAQN

CONSTRUCTION OF pAQN-EHX

CONSTRUCTION OF pEBSTC

CONSTRUCTION OF pEBST

Expresion vector, pEBST

```
                                    HindIII
-395                          AAGCTTATCTTGAAATGAATGATAAGGAAGGGGCG  -361

-360  ATTGAATTACTTGAAGAGGTAACGGCAAAAGCGGATGGGGCTGTAAAAGCGGAAGCTGAG  -301

-300  GAAGTTATTGAATAACTAATTTTTCAAATGTTCTGTTTTAAGGCCGTAAACGATTGAGTCT  -241

-240  CTTAAAGCGTACTATGTCATCATAAGGCTGGTGTGGCATAGTACGCACTTTTAATGATCT  -181

-180  TCATTATTTATTACTTATTGGTATGACAGTTTGTAAATAATAATTTTTCAATTGATATTT  -121
                              -35                           -10
-120  TTATGCTGGTATTGAACCTGAAATCAAATGAGATATATCTCACAAAAAGCAAATGTAAAC  -61

-60   ATCATCTTAAATAGATGAGGCAATATACTACTAAGAATTTTTTATGTGAATGTGCTTAAT  -1
                      SD
  1   ATGAAGAAAATACTGACAGTTCTATCTATTTTTATTCTTTCAGCGTGTAATAGTGACAAT  60
  1   M  K  K  I  L  T  V  L  S  I  F  I  L  S  A  C  N  S  D  N  20
                                    PstI
 61   ACCAGCTTGAAAGAAACGGTAAGCTCTAATTCTGCAGATGTAGTAGAAACAGAAACTTAC  120
 21   T  S  L  K  E  T  V  S  S  N  S  A  D  V  V  E  T  E  T  Y   40

121   CAACTGACACCGATTGATGCTCCTAGCTCTTTTTTATCTCATTCTTGGGAGCAAACATGT  180
 41   Q  L  T  P  I  D  A  P  S  S  F  L  S  H  S  W  E  Q  T  C   60
                                          EcoRV
181   GGCACACCTATCTTGAATGAAAGTGACAAGCAAGCGATATCTTTTGATTTTGTTGCTCCA  240
 61   G  T  P  I  L  N  E  S  D  K  Q  A  I  S  F  D  F  V  A  P   80
                                 DraI
241   GAGTTAAAGCAAGATGAAAAGTATTGTTTTACTTTTAAAGGTATTACAGGCGATCATAGG  300
 81   E  L  K  Q  D  E  K  Y  C  F  T  F  K  G  I  T  G  D  H  R  100

301   TATATCACAAATACAACATTAACTGTTGTTGCACCTACGCTAGAAGTTTACATCGATCAT  360
101   Y  I  T  N  T  T  L  T  V  V  A  P  T  L  E  V  Y  I  D  H  120
      EcoT22I
361   GCATCCTTACCATCGCTACAGCAGCTTATCCACATTATTCAAGCAAAAGATGAATACCCA  420
121   A  S  L  P  S  L  Q  Q  L  I  H  I  I  Q  A  K  D  E  Y  P  140

421   AGTAATCAACGTTTTGTCTCTTGGAAGCGTGTAACTGTTGATGCTGATAATGCCAATAAG  480
141   S  N  Q  R  F  V  S  W  K  R  V  T  V  D  A  D  N  A  N  K  160

481   TTAAACATTCATACTTATCCATTAAAAGGCAATAATACCTCACCAGAAATGGTGGCAGCG  540
161   L  N  I  H  T  Y  P  L  K  G  N  N  T  S  P  E  M  V  A  A  180

541   ATTGATGAGTATGCTCAGAGCAAAAATCGATTGAATATAGAGTTCTATACAAATACAGCT  600
181   I  D  E  Y  A  Q  S  K  N  R  L  N  I  E  F  Y  T  N  T  A  200

601   CATGTTTTTAATAATTTACCACCTATTATTCAACCTTTATATAATAACGAGAAGGTGAAA  660
201   H  V  F  N  N  L  P  P  I  I  Q  P  L  Y  N  N  E  K  V  K  220

661   ATTTCTCATATTAGTTTGTATGATGATGGTTCTTCTGAATATGTAAGTTTATATCAATGG  720
221   I  S  H  I  S  L  Y  D  D  G  S  S  E  Y  V  S  L  Y  Q  W  240

721   AAAGATACACCAAATAAGATAGAAACATTAGAAGGTGAAGTATCGCTTCTTGCTAATTAT  780
241   K  D  T  P  N  K  I  E  T  L  E  G  E  V  S  L  L  A  N  Y  260
            AccIII
781   TTAGCAGGAACATCTCCGGATGCACCAAAAGGAATGGGAAATCGTTATAACTGGCATAAA  840
261   L  A  G  T  S  P  D  A  P  K  G  M  G  N  R  Y  N  W  H  K  280

841   TTATATGACACTGATTATTACTTTTTGCGCGAAGATTACCTTGACGTTGAAGCAAACCTA  900
281   L  Y  D  T  D  Y  Y  F  L  R  E  D  Y  L  D  V  E  A  N  L  300
                                                      NcoI
901   CATGATTTACGTGATTATTTAGGCTCTTCCGCAAAGCAAATGCCATGGGATGAATTTGCT  960
301   H  D  L  R  D  Y  L  G  S  S  A  K  Q  M  P  W  D  E  F  A  320
```

Fig. 7

```
 961 AAATTATCTGATTCTCAGCAAACACTATTTTTAGATATTGTGGGTTTTGATAAAGAGCAA 1020
 321  K  L  S  D  S  Q  Q  T  L  F  L  D  I  V  G  F  D  K  E  Q   340

1021 TTGCAACAACAATATTCACAATCCCCACTACCAAACTTTATTTTTACCGGCACAACAACT 1080
 341  L  Q  Q  Q  Y  S  Q  S  P  L  P  N  F  I  F  T  G  T  T  T   360

1081 TGGGCTGGGGGGGAAACGAAAGAGTATTATGCTCAGCAACAAGTAAATGTGATTAATAAT 1140
 361  W  A  G  G  E  T  K  E  Y  Y  A  Q  Q  Q  V  N  V  I  N  N   380

1141 GCGATCAATGAAACTAGCCCTTATTATTTAGGTAAAGACTACGATCTATTTTTCAAGGGG 1200
 381  A  I  N  E  T  S  P  Y  Y  L  G  K  D  Y  D  L  F  F  K  G   400
                                                HindIII
1201 CATCCTGCTGGTGGCGTTATTAACGACATCATTCTTGGAAGCTTCCCTGATATGATCAAT 1260
 401  H  P  A  G  G  V  I  N  D  I  I  L  G  S  F  P  D  M  I  N   420

1261 ATTCCAGCCAAGATTTCATTTGAGGTCTTGATGATGACGGATATGTTGCCTGATACAGTA 1320
 421  I  P  A  K  I  S  F  E  V  L  M  M  T  D  M  L  P  D  T  V   440
                     SacI
1321 GCTGGTATTGCGAGCTCTCTGTACTTCACAATTCCTGCCGATAAAGTTAATTTTATTGTA 1380
 441  A  G  I  A  S  S  L  Y  F  T  I  P  A  D  K  V  N  F  I  V   460

1381 TTTACTTCATCTGACACTATTACTGATCGTGAAGAGGCTCTTAAATCACCATTAGTACAA 1440
 461  F  T  S  S  D  T  I  T  D  R  E  E  A  L  K  S  P  L  V  Q   480

1441 GTGATGCTAACGTTGGGTATTGTTAAAGAAAAAGATGTTCTGTTCTGGGCTGATCATAAA 1500
 481  V  M  L  T  L  G  I  V  K  E  K  D  V  L  F  W  A  D  H  K   500

1501 GTAAACTCGATGGAAGTTGCCATTGATGAAGCCTGTACTCGGATCATTGCAAAGCGACAA 1560
 501  V  N  S  M  E  V  A  I  D  E  A  C  T  R  I  I  A  K  R  Q   520

1561 CCAACCGCGAGTGATTTACGCTTGGTTATTGCTATTATCAAAACAATTACTGATCTTGAG 1620
 521  P  T  A  S  D  L  R  L  V  I  A  I  I  K  T  I  T  D  L  E   540

1621 CGTATTGGCGATGTGGCAGAAAGTATTGCTAAAGTCGCATTAGAGAGCTTTAGTAATAAG 1680
 541  R  I  G  D  V  A  E  S  I  A  K  V  A  L  E  S  F  S  N  K   560
                                    BalI         Nsp(7524)V
1681 CAATATAACCTATTGGTTTCTTTAGAATCTCTTGGCCAGCATACGGTTCGAATGCTGCAT 1740
 561  Q  Y  N  L  L  V  S  L  E  S  L  G  Q  H  T  V  R  M  L  H   580

1741 GAGGTGTTAGATGCGTTTGCTCGTATGGATGTTAAAGCCGCAATAGAAGTGTACCAAGAA 1800
 581  E  V  L  D  A  F  A  R  M  D  V  K  A  A  I  E  V  Y  Q  E   600
                                                         NdeI
1801 GATGATCGAATTGATCAAGAGTATGAGTCGATAGTCAGACAGCTAATGGCCCATATGATG 1860
 601  D  D  R  I  D  Q  E  Y  E  S  I  V  R  Q  L  M  A  H  M  M   620

1861 GAAGATCCAAGCTCAATTCCTAATGTAATGAAAGTGATGTGGGCGGCACGTTCTATTGAG 1920
 621  E  D  P  S  S  I  P  N  V  M  K  V  M  W  A  A  R  S  I  E   640

1921 CGAGTGGGTGATCGCTGTCAAAACATTTGTGAGTACATTATCTACTTTGTGAAGGGTAAA 1980
 641  R  V  G  D  R  C  Q  N  I  C  E  Y  I  I  Y  F  V  K  G  K   660

1981 GACGTTCGCCATACCAAACCAGATGATTTTGGTACTATGCTCGATTAATCTATACAAGAA 2040
 661  D  V  R  H  T  K  P  D  D  F  G  T  M  L  D  *               675

2041 ACAAGAAACAAGAAGGTCGCCAGCATCGTAAATGTGGCGACCTTTTTTAATGCAAAAAAG 2100

2101 CCCTTCTAAAGGTAAACGAAGGGCGAGAGTAACCAAATGGTCAAAATTGAGTGGATATAA 2160
                                                        HpaI
2161 CATTCATGCTGATTTTGTTATTGTTGCTATATTTCAATTAGTTAACTGCGTTTCAGTTAA 2220

2221 AGCTGTATTGTAAACCGACACCGCCTGCGACTTCTGATGACGAGTATTTACCGCTCGTTT 2280
                                         AflII
2281 CGTAATGGAAAGTTCCTGATACACTTAAGTTTTCGTTGATTCCATAAGCACCACCAAGGC 2340
     HindIII
2341 TAAAGCTT                                                     2348
```

Fig. 8

Growth of A2, B2, C2 vs Culture hours

β-GALACTOSIDE-α2, 6-SIALYLTRANSFERASE GENE

This application is the national phase under 35 U.S.C. §371 of prior PCT International Application No. PCT/JP98/00850 which has an International filing date of Mar. 2, 1998 which designated the United States of America, the entire contents of which are hereby incorporated by reference.

FIELD OF THE INVENTION

This invention relates to a novel gene encoding β-galactoside-α2,6-sialyltransferase.

Further, it relates to a gene encoding a novel signal peptide.

PRIOR ART

In recent years, biological activities of complex carbohydrates such as glycoptoteins and glycolipids have been successively clarified and the importance of sugar chains has come to be understood. Sialic acids are known as sugars often found at the nonreducing end of a sugar chain of complex carbohydrates. While the physiological functions and biological significance of sugar chains are important, it is considered that sialic acids have a particularly large number of functions. However, it is difficult to chemically synthesize these substances, in particular, to add a sialic acid to the chain of oligosaccharides, complex carbohydrates, etc. Accordingly, attention has been paid to enzymatic methods by which these products can be easily synthesized at a high yield without any side-reactions.

Sialyltransferases currently available on the market includes enzymes obtained from the submaxillary gland, liver, etc. of an animal such as rat, swine and human being [Poulson et al. J. Biol. Chem. 252, 2356–2362 1977), Weistein et al. J. Biol. Chem. 257, 13835–13844 (1982), Miyagi et al. Eur. J. Biochem. 126, 253–261 (1982)]. However, the enzymes from animals cannot be obtained in a large amount due to difficulties involving purification, which makes them highly expensive. Moreover, the poor stability of these enzymes is also a problem.

Under these circumstances, the present inventors conducted a search for a bacterium having sialyltransferase activity to provide a sialyltransferase which can be supplied in a large amount. As a result, they found that a marine bacterium Photobacterium damsela JT0160 (hereinafter referred to as "JT0160") has such an activity. Further, they purified the sialyltransferase 0160 (hereinafter referred to as "ST0160") produced by JT0160 to an electrophoretically homogeneous level. They furthermore analyzed the binding property of this enzyme and thus clarified that ST0160 is a 0-galactoside-α2,6-sialyltransferase which transfers sialic acids, via an α-2,6-linkage, to the 6-position of galactose at the nonreducing end of a sugar chain [JP (Kokai) Hei 8-154673]. Thus, it became possible to produce the sialyltransferase in a large amount by culturing JT0160 capable of producing ST0160. Since this enzyme is of the membrane-binding type, it is necessary in this process to add a surfactant in the purification of the enzyme, which gives rise to problems such as the possibile contamination of surfactants in the purified enzyme.

On the other hand, advances in genetic engineering techniques have made it possible to express certain proteins in large amounts with the use of recombinant Escherichia coli cells which have been transformed by an expression vector carrying the gene of a protein of interest. When this approach is applied to the production of β-galactoside-α2, 6-sialyltransferase, the problems described above can be solved and, moreover, it is possible to produce modified or non-native enzymes such as a soluble enzyme lacking the sequence which takes part in the membrane-binding of the protein, or an enzyme with a modified substrate specificity, etc. Furthermore, by using a highly efficient promoter such as T7 promoter, it becomes possible to construct a production system capble of delivering an extremely high productivity so that a desired protein amounts to 50% or more of the soluble proteins produced in microbial cells. However, a problem has existed that the genomic DNA of JT0160 could not be extracted from the culture in marine broth which has normally been employed as the growth medium. Thus no gene encoding the β-galactoside-α2,6-sialyltransferase has been obtained hitherto. That is to say, the β-galactoside-α2, 6-sialyltransferase was not available for use in genetic engineering before the present invention, in spite of existence of a strong demand.

SUMMARY OF THE INVENTION

An object of the present invention is to provide a novel gene encoding β-galactoside-α2,6-sialyltransferase.

Another object of the present invention is to provide expression vectors for producing the β-galactoside-α2,6-sialyltransferase protein containing the above-mentioned gene.

A further object of the present invention is to provide a process for producing recombinant β-galactoside-α2,6-sialyltransferase proteins by using the above-mentioned expression vectors.

A further object of the present invention is to provide recombinant β-galactoside-α2,6-sialyltransferase proteins produced by using the above-mentioned process.

A further object of the present invention is to provide a gene encoding a novel signal peptide.

BRIEF DESCRIPTIONS OF THE DRAWINGS

FIG. 7 (SEQ ID NO:2) shows the first half of the nucleotide sequence of the bst gene together with the deduced amino acid sequence thereof.

FIG. 8 (SEQ ID NO:2) shows the latter half of the nucleotide sequence of the bst gene together with the educed amino acid sequence thereof.

DETAILED DESCRIPTION OF THE INVENTION

Figure 1:
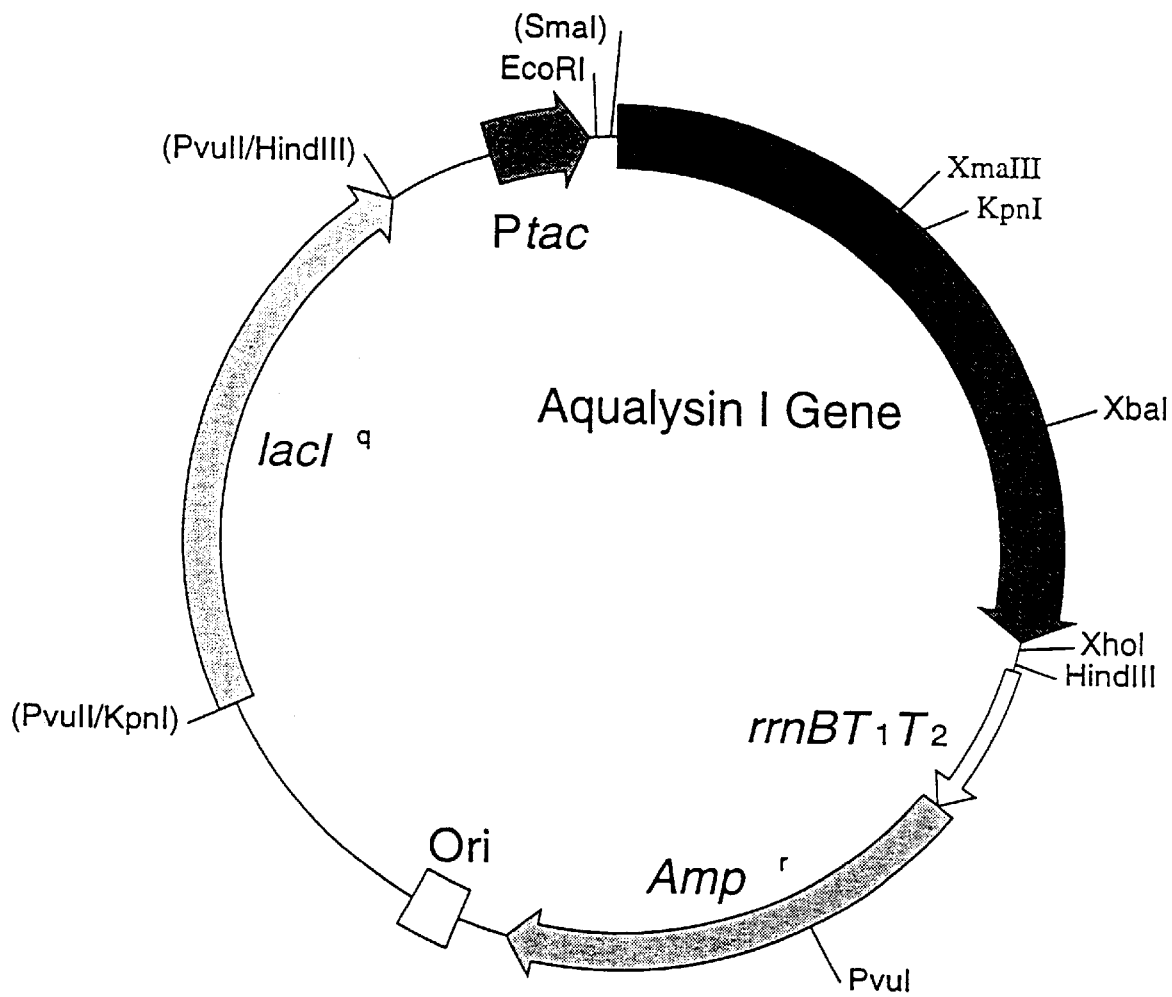
FIG. 1 illustrates the structure of pAQI.

As a result of extensive studies, the present inventors have succeeded for the first time in extracting genomic DNA from JT0160 by growing JT0160 not on Marine Broth 2216 (manufactured by Difco) but Nutrient Broth (manufactured by Oxoid). Further, they have attempted to isolate the gene encoding the ST0160 protein (hereinafter referred to as "bst gene") from the DNA thus extracted. In spite of various difficulties including the fact that the ST0160 protein is potentially toxic to commonly employed host cells, bst gene has been successfully isolated. Further, the nucleotide sequence of the gene has been determined along with the deduced amino acid sequence. The ST0160 protein has the amino acid sequence represented by SEQ ID NO:1 as in Sequence Listing.

The present inventors have further constructed expression vectors containing the gene thus obtained and succeeded in the expression of the recombinant ST0160 protein.

The present invention will now be described in greater detail.

β-Galactoside-α2,6-sialyltransferase

The term "β-galactoside-α2,6-sialyltransferase" as used herein means a protein having an activity of transferring sialic acid from cytidine monophosphate-sialic acid to the 6-position of a galactose residue in the sugar chain of a complex or free carbohydrate, or to the 6-position of a monosaccharide which is capable of constituting complex carbohydrates and having a hydroxyl group on the carbon atom at the 6-position. This enzyme has an optimum pH value within a range of from 5 to 6, the optimum temperature of 30° C. and a molecular weightdetermined by gel filtration of 64,000±5,000, though the present invention is not bound by these figures. Examples of the above-mentioned monosaccharide capable of constituting complex carbohydrates and having a hydroxyl group at the carbon atom of 6-position include galactosamine, mannose and N-acetylgalactosamine mannose.

The β-galactoside-α2,6-sialyltransferase encoded by the gene of the present invention was discovered in Photobacterium damsela JT0160. It has been revealed that the same enzyme is also contained in Photobacterium damsela ATCC33539 and Photobacterium damsela ATCC35083. Thus, it is expected that this enzyme is also produced by other microorganisms or organs.

β-Galactoside-α2,6-sialyltransferase gene

The nucleotide sequence of the bst gene determined in the present invention is shown in SEQ ID NO:2 and FIGS. 7 and 8 together with the deduced amino acid sequence encoded thereby. As this SEQ ID NO:2 shows, the DNA of the gene comprises 2028 base pairs in total (i.e., nucleotide Nos. 396 to 2420). The sequence of nucleotide Nos. 396 to 398 corresponds to the initiation codon while that of nucleotide Nos. 2421 to 2423 corresponds to the termination codon. The sequence (*) of nucleotide Nos. 2421 to 2423 (i.e., TAA) may be replaces by TGA or TAG. Further, the DNA contains a region highly homologous with the promoter sequence (−10 and −35 regions, nucleotides 386 and 361 of SEQ ID NO:2) and the ribosome-binding region (SD sequence) of *E. coli* in the 5' upstream of the structural gene as shown in FIGS. 7 and 8. Also, a stem and loop structure which constitutes a typical terminator region was observed in the 3' downstream of this structural gene. It is considered that these are the regions which regulate the expression of the bst gene.

SEQ ID NO:1 represents the amino acid sequence of the ST0160 protein. The ST0160 protein is composed of 675 amino acid residues in total including a signal sequence consisting of 15 amino acid residues (Nos. 1–15 in SEQ ID NO:1) and an extracellular region (Nos. 16–498 in SEQ ID NO:1). The protein, having the amino acid sequence deduced on the basis of the bst gene, has a molecular weight of 76.5 kDa, while the molecular weight thereof excluding the signal sequence is 74.8 kDa. Since the molecular weight determined by SDS electrophoresis of a substantially pure ST0160 protein is about 61 kDa [JP(Kokai) Hei 8-154673], it is considered that the ST0160 protein is processed into the active form or vulnerable to an intracellular protease during the purification.

The C-terminal region (Nos. 497–675 in SEQ ID NO:1) has the significanly high homology of 60% or above with the phosphate transport system-regulating protein of *E. coli*. It is indicated that two long α-helix structures accompanied by a short turn structure in-between are located at the 539to 594-residues in this region. Assuming that, in general, an α-helix unit has 18 amino acid residues, the ST0160 protein carries the two consecutive α-helix units in such a manner that, in each unit, all the four amino acids constituting one face are hydrophobic. In addition, there is a region having predominantly hydrophobic amino acid residues in the C-terminal region. No region which is potentially bindable to membranes is detected exept for the above-mentioned region and the signal sequence region at the N-terminal, it is considered that the above region is the membrane-binding region of ST0160. Thus, the ST0160 protein is completely different from sialyltransferases of animal origin in terms of the manner in membrane-binding, since it is considered that the membrane-binding regions of the sialyltransferases of animal origin cloned so far is located in the N-terminal region.

When these facts are taken into consideration, it is apparent that the protein has enzymatic activity even when at least a part of the membrane-binding region and/or the signal sequence region of the ST0160 protein has been deleted. Therefore, genes encoding such proteins are also included in the present invention. In particular, a β-galactoside-α2,6-sialyltransferase which is soluble due to the deletion of the membrane-binding region of the ST0160 protein is a prefered embodiment of the present invention, as will be described in detail hereinafter.

As will be described in the following Examples, the gene of the present invention can be obtained from a gene library formed by using the genomic DNA of JT0160 grown in, for example, Nutrient Broth (manufactured by Oxoid) by, for example, the plaque hybridization method. Alternatively, it can be easily prepared by the PCR method with the use, as a template, of a gene library originating in a microorganism, etc. based on the nucleotide sequence of the DNA determined in the present invention.

Further, the β-galactoside-α2,6-sialyltransferase gene thus prepared can be modified into mutants thereof by the following methods.

A single amino acid is encoded by two or more codons. Therefore, any DNA encoding the amino acid sequence represented by SEQ ID NO:1 or the part thereof having the enzyme activity is included in the present invention.

Moreover, it is well known that the physiological activity of a peptide will be maintained even though the amino acid sequence of the peptide is somewhat modified, i.e., one or more amino acids therein are substituted or deleted therefrom or one or more amino acids are added thereto. For example, a mutant may contain a conservatively substituted amino acid sequence. The expression "conservatively substituted" means that specific amino acid residue(s) have been substituted by other residue(s) which are similar in the physiological characteristics. Nonlimiting examples of conservative substitution include the substitution among aliphatic group-containing amino acid residues (for example, Ile, Val, Leu and Ala) and the substitution among polar group-containing amino acid residues (for example, Lys and Arg). Therefore, the present invention includes in its scope mutants of the β-galactoside-α2,6-sialyltransferase which have the amino acid sequence represented by SEQ ID NO:1 or an enzyme active part thereof having been modified in the above-mentioned manner and yet maintain the biological activity of the β-galactoside-α2,6-sialyltransferase. Moreover, DNAs encoding these mutant proteins are included in the present invention.

A mutant having the addition, deletion or substitution of amino acid(s) can be formed by, for example, subjecting the DNA encoding the same to the site-specific mutagenesis which is well known technique (see, for example, Nucleic Acid Research, Vol. 10, No. 20, p. 6487–6500, 1982). The expression "one or more amino acids" as used herein means amino acids in such a number as to allow the addition, deletion or substitution thereof by the site-specific mutagenesis method.

The site-specific mutagenesis can be carried out in the following manner by using, for example, a synthetic oligonucleotide primer complementary to the single-strand DNA to be mutated except certain mismatches at the point to be mutated. Namely, the above-mentioned synthetic oligonucleotide is used as the primer for synthesizing a strand complementary to a phage. Then host cells are transformed by the double-strand DNA thus obtained. The culture of the transformed bacterium is plated on an agar plate and plaques are formed from a single cell containing the phage. Theoretically 50% of newly formed colonies will contain the mutated phage as a single strand, while the other 50% of the colonies will have the original sequence. Next, the obtained plaques are hybridized with a synthetic probe labeled with kinase at a temperature where those DNAs completely identical with the DNA having the above-mentioned desired mutation will hybridize while those having the original strand will not. Next, the plaques hybridized with the probe are taken up and cultured to recover the DNA.

In addition to the site-specific mutagenesis method as described above, methods for substituting, deleting or adding one or more amino acids to the amino acid sequence of a biologically active peptide such as an enzyme while maintaining its activity include: a method wherein a gene is treated with a mutagen and a method comprising selectively cleaving a gene, and then deleting, adding or substituting specific nucleotide(s) followed by ligation.

Furthermore, the nucleotide sequences within the scope of the present invention include isolated DNAs and RNAs which are hybridizable with the β-galactoside-(2,6 -sialyltransferase nucleotide sequence disclosed herein under conditions with mild or severe stringency and encode the biologically active β-galactoside-α2,6-sialyltransferase. The expression "conditions with mild stringency" for hybridization means those described in Sambrook et al., "Molecular Cloning: A Laboratory Manual", 2 ed., Vol. 1, pp. 1.101–104, Cold Spring Harbor Laboratory Press (1989). As Sambrook et al. define, the conditions with mild stringency involve use of a prewashing solution (5×SSC, 0.5% SDS and 0.1 mM EDTA) (pH 8.0) and hybridization performed at about 55° C., 5×SSC overnight. The conditions with severe stringency involve hybridization performed at a higher temperature and washing. The temperature and the salt concentration of the washing solution may be appropriately selected depending on various factors such as the size of probe. It is prefered to effect the hybridization at a concentration of 5×SSC or below at a temperature of 20° C. or above.

Production of recombinant β-galactoside-α2,6-sialyltransferase

The present invention also provides expression vectors containing the β-galactoside-α2,6-sialyltransferase gene and a process for producing the recombinant β-galactoside-α2, 6-sialyltransferase protein which comprises culturing host cells containing the expression vector under conditions appropriate for the expression of the above-mentioned gene and recovering the recombinant protein thus expressed.

To produce the recombinant β-galactoside-α2,6-sialyltransferase protein of the present invention, the β-galactoside-α2,6-sialyltransferase gene sequence is linked to appropriate transcription or translation regulating nucleotide sequences derived from genes of mammals, microorganisms, viruses, insects, etc., and they are inserted into an expression vector selected depending on the host cells to be used. The regulating sequences are exemplified by transcription promoters, operators or enhancers, mRNA ribosome-binding sites and appropriate sequences controlling the initiation or termination of the transcription or translation.

Examples of host cells appropriate for the expression of β-galactoside-α2,6-sialyltransferase protein include prokaryotic cells, yeasts and higher eukaryotic cells. Cloning and expression vectors appropriately employed in host cells of bacteria, fungi, yeasts and mammals are described in, for example, Pouwels et al., "Cloning Vectors: A Laboratory Manual, Elsevier, New York, (1985).

Prokaryotes include gram-negative and gram-positive bacteria such as *E. coli* and *Bacillus subtilis*. When a prokaryote such as *E. coli* is used as a host, the β-galactoside-α2,6-sialyltransferase protein may contain the N-terminal methionine residue so as to facilitate the expression of the recombinant polypeptide in the prokaryotic cells. After the completion of the expression, this N-terminal Met can be deleted from the recombinant β-galactoside-α2,6-sialyltransferase protein.

An expression vector to be used in prokaryotic host cells generally contains one or more phenotypic selective marker genes which impart, for example, tolerance to an antibiotic or auxotrophy to the host. Examples of the expression vectors suitable for prokaryotic host cells include commercially available plasmids such as pBR322 (ATCC37017) and those derived therefrom. Plasmid pBR322 contains ampicillin- and tetracycline-resistence genes, which facilitates identification of transformed cells. An appropriate promoter and the DNA sequence of the β-galactoside-α2, 6-sialyltransferase gene are inserted into pBR322 vector. Other examples of commercially available vectors include pKK223-3 (manufactured by Pharmacia Fine Chemicals, Upsala, Sweden) and pGEM1 (manufactured by Promega Biotec, Madison, Wis.).

Examples of promoter sequences commonly employed in expression vectors for prokaryotic host cells include tac promoter, β-lactamase (penicillinase) and lactose promoter (Chang et al., Nature 275:615, 1978; and Goeddel et al., Nature 281:544, 1979). A particularly useful prokaryotic host cell expression system is one with the use of phage λP$_L$ promoter and cI857ts heat labile repressor sequence. Examples of plasmid vecotrs having a derivative of λP$_L$ promoter and available from American Type Culture Collection include plasmid pHUB2 contained in *E. coli* JMB9 (ATCC370929) and pPLc28 contained in *E. coli* RP1 (ATCC53082).

As will be described hereinafter, it was impossible to obtain *E. coli* having a plasmid carrying the HindIII fragment (about 2.8 kbp) containing the whole bst gene. instead, this gene was cloned as two HindIII fragments (about 1.6 kb and about 1.2 kb). In view of these facts, the protein produced by this gene may be fatal to E. coli. Therefore, in order to express this gene, use of a regulatable promoter is prefered so as to express the bst gene after the host has been sufficiently grown. A typical example of the regulatable promoter is tac promoter, though the present invention is not limited thereto. Further, the present inventors have found that the expression is weakened by placing tac promoter at a point which is, for example, several bases away from the initiation codon of the bst gene. The interval between the promoter and the initiation codon can be appropriately varied in a conventional manner.

Also, the recombinant β-galactoside-α2,6-sialyltransferase proteins may be expressed in yeast host cells. Although it is prefered to use yeasts belonging to the genus Saccharomyces (for example, S. cerevisiae), use may be made of those belonging to other genera such as Pichia and Kluyveromyces. Yeast vectors usually contain a sequence from the replication origin of 2μ yeast plasmid, an autonomously replicating sequence (ARS), a promoter region, a polyadenylation sequence, a sequences for terminating transcription and selective marker gene(s). The recombinant β-galactoside-α2,6-sialyltransferase proteins can be secreted by using the leader sequence of yeast a factor. Moreover, there are known other leader sequences suitable for promoting the secretion of recombinant polypeptides from yeast hosts. Yeasts can be transformed by the methods described in, for example, Hinnen et al., Proc. Natl. Acad. Sci. USA 75:1929, 1978.

The recombinant β-galactoside-α2,6-sialyltransferase proteins can be expressed by using mammalian or insect host cell culture systems. Instead, established cell lines originating from mammals may be used.

Transcriptional and translational regulatory sequences for mammalian host cell expression vectors can be obtained from virus genomes. Commonly employed promoter sequences and enhancer sequences are derived from polyoma virus, adenovirus 2, etc. To express the structural gene sequence in mammalian host cells, other genetic elements from SV40 virus genomes may be used, which are, for example, replication origin of SV40, early and late promoters, enhancers, splicing sites and DNA sequences from polyadenylation sites. Expression vectors to be used in mammalian host cells can be constructed by, for example, the method of Okayama & Berg (Mol. Cell. Biol. 3:280, 1983).

A process for producing the β-galactoside-α2,6-sialyltransferase protein of the present invention comprises culturing host cells transformed by an expression vector containing the DNA sequence encoding the β-galactoside-α2,6-sialyltransferase protein under such conditions as to allow the expression of this protein and then recovering the β-galactoside-α2,6-sialyltransferase protein from the culture medium or cell extract depending on the expression system employed. Procedures for purifying a recombinant β-galactoside-α2,6-sialyltransferase protein may be appropriately selected by considering several factors, for example, the type of the host cells employed, whether the protein is secreted into the culture medium or not, etc.

Soluble β-galactoside-α2,6-sialyltransferase

In another aspect, the present invention provides soluble β-galactoside-α2,6-sialyltransferase proteins and genes encoding said protein. Such a soluble β-galactoside-α2,6-sialyltransferase protein contains the whole extracellular domain of the natural β-galactoside-α2,6-sialyltransferase protein or a part thereof but lacks the membrane-binding region which binds the polypeptide on cell membranes. For example, the above-mentioned ST0160 protein can be solubilized by deleting the entire or a a portion of the amino acid residues in the region between 499- and 675-positions. Immediately after the synthesis, the soluble β-galactoside-α2,6-sialyltransferase protein may contain a natural or heterogenous signal peptide. In that case, however, the signal peptide should be separated when the β-galactoside-α2,6-sialyltransferase protein is secreted from cells. The present invention includes any soluble protein from which the membrane-binding region and/or the signal peptide region have been entirely or partly deleted so long as it maintains the β-galactoside-α2,6-sialyltransferase activity. That is to say, the soluble β-galactoside-α2,6-sialyltransferase protein may contain a part of the membrane-binding region, a part of the cytoplasmic region or other sequences provided that the protein is enzymatically active. Such soluble proteins can be easily purified when produced by host cells, since they do not bind to cell membranes. Signal peptides for secreting the proteins may be derived from either the host organism or a heterogenous one. The amino acid sequence between the 1- and 15-positions in SEQ ID NO:1 is a prefered signal peptide.

Truncated β-galactoside-α2,6-sialyltransferases comprising a soluble protein can be prepared by using any of the techniques known in the art. For example, the full-length cloned DNA fragment of SEQ ID NO:2 is cleaved with a restriction enzyme to give truncated DNA fragments which are then isolated by electrophoresis on agarose gel. In this process, the full-length DNA fragment may be cleaved with a restriction enzyme either at a site occurring in nature or at the restriction site of the linker which is contained in the DNA fragment of SEQ ID NO:2. The DNA sequence encoding a truncated protein fragment thus isolated can be amplified by the well known polymerase chain reaction. Alternatively, a termination codon may be introduced at an appropriate place which is, for example, immediately downstream of the codon of the final amino acid of the extracellular region, by way of a known mutagenesis method.

Another method comprises deleting nucleotides from the terminal region of the DNA fragment by a treatment with an enzyme (for example, Ba131 exonuclease) and substitute them with a fragment to provide a desired end. Linkers useful in this approach are commercially available. They include those which can be linked to the blunt end generated by the digestion with Ba131 and have a restriction endonuclease cleavage site.

It is also possible to prepare a synthetic oligonucleotide, which is linked to the DNA fragment to create an N- or C-terminal at a desired point in the recombinant protein. To facilitate gene manipulation, the oligonucleotide may contain a restriction site in the upstream of the coding sequence, or it may carry an initiation codon (ATG) at the N-termial thereof for the expression of the protein in a specific host.

The soluble proteins can be obtained by culturing host cells transformed by the obtained genes and then purifying the culture supernatant. To elevate the yield, it is prefered to disrupt the cells.

To illustrate the specific embodiments of the present invention, and not by way of limiting the technical scope thereof, the following Examples are given.

Methods employed, in the Examples below, were as follows:

Amino Acid Sequence Analysis of Peptides

Amino acid sequences of peptides were analyzed by Protein sequencer model 476A (Perkin Elmer Co.).

Synthesis of Probes

Regions which comprised as many amino acids having a smaller number of codon degeneration as possible were selected from within the amino acid sequence of a protein to be probed, and the nucleotide sequences deduced from these amino acid sequences were synthesized. The synthesis was carried out by Japan Bio-service.

Construction of JT0160 Gene Library

JT0160 was grown in nutrient broth (Oxoid Co.) at 30° C. for 16 hr, and the cells were collected by centrifugation (8,000 rpm for 10 min at 4° C.). Genomic DNA was isolated from 3 g of these cells by the method of Saito and Miura (Preparation of transforming deoxyribonucleic acid by phenol treatment. Biochim. Biophys. Acta 72, 619–629 (1963)). Fifty $\mu$g of the purified genomic DNA was partially digested with Sau3AI, and the resulting gene fragments were linked to KDASH II/BamHI vector kit (product of Stratagene Co.). These were packaged by using GigapakII packaging extracts (Stratagene Co.), to construct a gene library.

Amplification of Gene Library

*Escherichia coli* XL-1 Blue MRA (P2) was employed as the host organism to amplify the constructed gene library. The organism was grown on LB medium under shaking at 150 rpm at 37° C., and then the culture was diluted with 10 mM magnesium chloride to a reading of 0.5 at $O.D._{660}$. Ten $\mu$g of the gene library preparation was added to 600 $\mu$l of this diluted bacterial suspension, and incubated at 37° C. for 15 min under shaking. The suspension was mixed with 10 ml of LB top agarose prewarmed at 48° C., which was overlaid onto LB plates prewarmed at 37° C. The plates were solidified at room temperature and incubated at 37° C. for 8 hr. After the host organism on the top agarose was completely lyzed, 5 ml of SM buffer was added to the plates, and they were allowed to stand for 15 min. Then, the top agarose was scraped off by a spatula together with the SM buffer and centrifuged (8,000 rpm for 10 min at 4° C.) to give a supernatant solution which was used as an amplified gene library.

Fluorescence Labeling of Probe

The synthesized probes were labeled with fluorescence by using 3'-Oligolabeling kit (product of Amersham).

Hybridization

A replica on agarose gel for Southern hybridization was prepared as follows:

DNA was digested with restriction endonuclease(s) and fragments were separated by electrophoresis on 0.8% agarose gel in TAE buffer. After the electrophoresis, the agarose gel was soaked in a denaturation solution (0.5 M NaOH and 1.5 M NaCl) for 15 min to allow the DNA fragments in the gel to be denatured with the alkali. Then, the gel was soaked in a neutralization solution (0.5 M Tris-HCl (pH 7.5), 1.5 M NaCl) for 5 min to neutralize the alkali. The gel was overlayed on a sheet of HybondN$^+$ of the same size, which was sandwiched between sheets of Kim paper towel and placed at room temperature to allow the DNA to transfer to the HybondN$^+$, to thereby form a replica on the gel. The replica was washed with 2×SSC buffer and placed to dry on filter paper at room temperature. Thereafter, the replica was baked at 80° C. for 2 hrs.

A replica of colonies or plaques for colony hybridization or plaque hybridization was prepared according to the following procedures:

A sheet of HybondN$^+$ was placed on an agar plate carrying an appropriate number of colonies or plaques, whereby the colonies or plaques were transferred to the sheet to give a replica. The master plate was stored at 4° C. after this replication. The replica was placed for 5 min on filter paper that had been wetted with a denaturation solution (0.5 M NaOH, 1.5 M NaCl), to thereby denature the colonies or plaques in alkali. The replica was neutralized on filter paper that had been wetted with a neutralization solution (0.5 M Tris-HCl (pH 7.5), 1.5 M NaCl) for 3 min, washed with 2×SSC buffer and left to dry on filter paper. Thereafter, the replica was baked at 80° C. a for 2 hrs.

Hybridization was performed by using 3'-Oligolabeling kit (Amersham) according to the attached manual, as follows:

The replica was placed in Hybribag containing 30 ml of Hybridization solution, followed by shaking in a water bath at 43° C. for 1 hr until equilibration was reached. Next, this solution received a fluorescence-labeled probe to give a concentration of 10 ng/ml, and was shaken in a water bath at 43° C. for 3 hr, to effect annealing. The procedures described below were carried out in a tray. After completion of the annealing, the replica was washed twice with 5×SSC containing 0.1% Triton X-100 for 5 min at room temperature. Then, it was washed twice with 1×SSC containing 0.1% Triton X-100 at 43° C. for 15 min and once again with buffer 1 (0.1 M Tris-HCl (pH 7.5), 1.5 M NaCl) for 1 min. The replica was soaked in a blocking solution and shaken for 30 min at room temperature. Thereafter, the replica was washed with buffer 1 for 1 min. Then, the replica was soaked in an appropriate antibody solution and shaken for 30 min at room temperature to effect binding of the antibody. The replica was washed four times with buffer 2 (0.1 M Tris-HCl (pH 7.5), 0.4 M NaCl) for 5 min. The replica was shaken in a detection solution for 1 min until fluorescence developed. It was then sandwiched between sheets of Kim paper towel to briefly remove water, and thereafter placed in a film cassette. A sheet of transparent polymer film (Saran wrap) and then an X ray film were overlaid thereon, and the X ray film was exposed for 15 min. The film was then developed by Fuji medical film processor (Fuji Film Co.).

Isolation of Phages Containing Bst Gene Fragment

Plaques showing desired properties were isolated from the agar plate, suspended in SM buffer (50 $\mu$l), and stored at 4° C. The phages extracted with SM buffer were amplified by the method described above in "Amplification of gene library".

Purification of Phage DNA

Phage DNA was purified from the amplified phage suspension by using $\lambda$-prepDNA Purification kit (Promega Biotec) as follows:

Forty $\mu$l of Nuclease mix was added to 10 ml of the amplified phage suspension, vortexed, and allowed to stand at 37° C. for 15 min, to decompose nucleic acids in the solution. The phage particles were precipitated by being left to stand on ice for 30 min after addition of 4 ml of a phage precipiting solution. The precipitate formed was collected by centrifugation (10,000 rpm for 10 min at 4° C.), which was resuspended in 500 $\mu$l of a phage buffer. This phage suspension was centrifuged (15,000 rpm for 5 min at 4° C.) to remove insoluble debris. One ml of DNA purification solution was added to this supernatant in-order to extract phage DNA by denaturing the phage proteineous components, and to allow the extracted DNA to be adsorbed on the resin at the same time. The suspension was transferred by syringe to provide a DNA purification column packed with the resin. The column was washed with 2 ml of 80% isopropanol and then centrifuged (12,000 rpm for 20 sec at 4° C.) to bring the resin to dryness. The phage DNA was eluted from the resin by adding 100 $\mu$l of prewarmed TE buffer at 80° C. to the column and then centrifuging the column at 12,000 rpm for 20 sec at 4° C.

Insertion of Gene Fragments into Vector

Plasmid pUC19 was digested with HindIII at 37° C. for 1 hr, treated with bacterial alkaline phosphatase (BAP) at 65° C. for 1 hr, and then precipitated with 70% ethanol. The precipitate was washed with 70% ethanol, dried in a Speedbag to remove ethanol, and dissolved in sterile water.

The purified phage DNA (5 μg) was digested with HindIII and applied to agarose gel electrophoresis. After the electrophoresis, the portion of the gel which contained the target gene fragments hybridized to the probe in Southern hybridization was cut out. The DNA was extracted from this gel piece with Geneclean (Funakoshi Co.), and was precipitated with ethanol. The precipitate was washed with 70% ethanol, dried with Speedbag tor remove ethanol, and dissolved in 10 μl of sterile water.

The DNA solution from the gel piece (9 μl) was mixed with the pUC19 (1 μl) that had been treated with HindIII and successively with BAP. Subsequently, Takara ligation kit solution I (10 μl) was added, and the mixture was vortexed, and incubated overnight at 16° C.

Transformation

Transformation of E. coli MV1184 was carried out as follows:

Plasmid DNA (10 μl) was added to competent cells of E. coli MV1184 (100 μl) that had been stored at −80° C. and thawed on ice. The mixture was placed on ice for 30 min, heated at 42° C. for 1 min, and again placed on ice for 3 min. To this, 900 μl of prewarmed LB broth was added and shaking was conducted at 37° C. for 1 hr. Then, an aliquot of the bacterial suspension was spread on an agar plate containing LB, ampicillin, IPTG, and X-Gal. The agar plate was incubated at 37° C. for 16 hr.

Isolation of Plasmid DNA

Colonies were picked up from the agar plate, seeded, and incubated in LB-ampicillin broth under shaking at 37° C. for 16 hr. The propagated cells were harvested by centrifugation (15,000 rpm for 10 min at 4° C.), from which plasmid DNA was purified by using a QIAGEN Mini-preparation kit.

DNA Nucleotide Sequence Analysis

Nucleotide sequences were analyzed by ALFred sequencer for the gene fragments that were inserted into a plasmid or phage. Plasmid samples for nucleotide sequence analysis were prepared according to the protocol attached to the cy5 Autoread sequencing kit (Pharmacia), and analysis was conducted with this kit. Fhage samples of nucleotide sequence analysis were prepared according to the protocol attached to Autocycle sequencing kit (Pharmacia), and analysis was conducted with this Autocycle sequencing kit.

Gel electrophoresis for nucleotide sequence analysis was conducted on a 0.5-mm long ranger gel according to the conditions given for this 0.5-mm long ranger gel electrophoresis.

Deposit

Photobacterium damsela JT0160 was deposited under the accession number FERM BP-4900, on November 24, 1994, at National Institute of Bioscience and Human Technology, Agency of Industrial Science and Technology, Japan.

EXAMPLE 1

Isolation of Bst Gene

The bst gene was cloned from the JT0160 library by using a probe designed from the ST0160 protein whose amino acid sequence was determined.

I. Isolation of 5'-Terminal Fragment of Bst Gene a. Trypsin digestion of ST0160 protein A 5 μg aliquot (1 ml) of a substantially pure ST0160 preparation was pipetted into a 1.5 ml siliconized tube, to which was added 150 μl of 100% TCA. The mixture was left to stand on ice for 20 min to precipitate the enzyme, and centrifuged at 15,000 rpm for 15 min at 4° C. The precipitate was washed twice with cold acetone and then dried in Speedbag. To this dried material, 25 μl of a mixture of 8 M urea and 0.4 M ammonium bicarbonate was added, and then 2.5 μl of 45 mM dithiothreitol was added. The mixture was incubated at 50° C. for 15 min to cleave any disulfide bonds in the peptides. The mixture was cooled to room temperature and the resulted SH groups were modified by addition of 2.5 μl of 100 mM iodoacetamide and standing the mixture for 15 min at room temperature. To this, 70 μl of super pure water and calcium chloride at a final concentration of 5 mM were added, followed by 5 U of trypsin in 10 μl. The mixture was incubated for trypsin digestion at 37° C. for 24 hr.

b. Isolation of Peptides

Peptides from the trypsin-digested ST0160 were fractionated as follows:

SmartSystem (Pharmacia) equipted with a column μRPCC2/C18SC2.1/10 (Pharmacia) was employed for isolation of the peptides. The trypsin-digested ST0160 was applied to the column, and the peptide fractions were collected with a gradient of solution 1 (0.06% TFA, 2% acetonitrile) and solution 2 (0.052% TFA, 100% acetonitrile) changing from 100% of solution 1 to 50% of solution 2 in 180 min.

c. Amino Acid Sequence Analysis of ST0160 Protein

The amino acid sequences were determined for a total of 10 peptides, ie. a peptide of the N-terminal region as well as 9 peptides presumably derived from the internal regions of the ST0160 enzyme by trypsin digestion. These amino acid sequences are shown in Table 1.

TABLE 1

| | | | |
|---|---|---|---|
| (a) | XNSDNTSLKETVSSXXAXV | (N-terminal sequence) | (SEQ ID NO:13) |
| (b) | DYLGSSAKK | (internal sequence) | (SEQ ID NO:14) |
| (c) | FVSWKIVN | (internal sequence) | (SEQ ID NO:15) |
| (d) | ANYLAGTSPDAPK | (internal sequence) | (SEQ ID NO:16) |
| (e) | ETVXXNSAVVVETETY | (internal sequence) | (SEQ ID NO:17) |

TABLE 1-continued (f) YNWHK         (internal sequence)   (SEQ ID NO:18)

(g) QAISFDFVAPELK (internal sequence)   (SEQ ID NO:19)

(h) QLIHIIQAK     (internal sequence)   (SEQ ID NO:20)

The N-terminal amino acid could not be determined; probably due to the fact that it was either in the form of a modified amino acid or a Cys residue.

d. Synthesis of Probes

A probe (probe A) was synthesized from the amino acid sequence (d) (corresponding to the amino acid residues 258–270 in SEQ ID NO: 1) selected from among the determined internal sequences. Probe A had the following sequence:

5'-GCIAAITAIITIGCIGGIACIIIICCIGAIGCICCIAA-3' (SEQ ID NO: 3)

herein, I stands for inosine which can recognize and form a base pair with adenine, uracil or cytosine.

e. Southern Hybridization of Genomic DNA

By using probe A synthesized above in section d, Southern hybridization was carried out against a HindIII-digested genomic DNA of P. damsela JT0160. A DNA fragment of approximately 2.8 kbp was observed to hybridize intensely with the probe. After agarose gel electrophoresis of the HindIII-digested genomic DNA, a portion of the gel which contained the 2.8 kbp DNA was cut out to extract the DNA. The extracted DNA was ligated to pUC19 which had been digested with HindIII and subsequently with BAP. E. coli MV1184 was transformed with this plasmid and subjectd to Colony hybridization. Unexpectedly, none of the colonies hybridized with probe A.

f. Isolation of Phases Supposedly Containing Bst Gene Fragments

Because no colony of interest was found by the colony hybridization in section d above, the library of P. damsela JT0160 genomic DNA was subjected to plaque hybridization with the probe. Then, 7 phage clones were obtained which probably contained a bst gene fragment. The phage DNA was isolated from each of the clones after they were propagated. The DNA was digested with HindIII and applied to Southern hybridization. As a result, a DNA fragment of approximately 1.6 kbp from all the clones hybridized intensely with probe A.

g. Subcloning

One clone, selected out of the 7 phage clones, was analyzed by agarose gel electrophoresis using 5 μg of its DNA digested with HindIII. After electrophoresis, the gel was cut out and the DNA was extracted from the portion that contained a DNA fragment of approximately 1.6 kbp. The extracted DNA was ligated to pUC19 that had been digested with Hind III and successively with BAP. The resulted plasmid was used to transform E. coli MV1184. Colony hybridization gave 3 colonies which strongly hybridized with probe A. These 3 colonies were picked up from the agar plate, separately seeded, and propagated in LB-ampicillin broth at 37° C. under shaking for 16 hr. The cells were harvested by centrifugation, from which plasmid DNA was prepared. The plasmid DNA was digested with HindIII and subjected to agarose gel electrophoresis. The results confirmed that the plasmids from all the 3 clones contained the DNA insert of an approximately 1.6 kbp fragment. When the gel, after the electrophoresis, was analyzed by Southern hybridization with the use of probe A, the 1.6 kbp DNA fragment hybridized strongly with the probe. Therefore, this fragment in the plasmids was considered to contain a segment of the bst gene.

h. Analysis of the 5'-Terminal Nucleotide Sequence of Bst Gene

The DNA fragment of approximately 1.6 kbp, that was cloned in the plasmids in section g, was analyzed for the nucleotide sequence by using ALFred DNA sequencer (nucleotide sequence from 35 to 1639 in SEQ ID NO:2). The amino acid sequence estimated from the nucleotide sequence revealed a long open reading frame (ORF) that consisted of 414 amino acid residues, starting at the 396th ATG (Met residue) from the HindIII recognition site and extending to another HindIII recognition site downstream. Comparison between the amino acid sequence deduced for this ORF and that determined chemically for ST0160 in section c identified the 8 amino acid residues in the N-terminal region.

Accordingly, the ORF was considered to comprise the 5'-terminal of the bst gene. The plasmid was named pBSTN.

However, the molecular weight 60 kDa of ST0160 indicated the necessity of further cloning in search of the 3'-terminal region of the bst gene that encodes at least 200 amino acid residues in the C-terminal side of ST0160 protein.

The sequence starting from the Asn residue, the 2nd amino acid in ST0160 N-terminal, coincided with the sequence starting from 17th amino acid in the ORF, so that it was considered that the N-terminus of ST0160 starts from the Cys residue as first suggested in section c. Hydrophobicity-hydrophilicity analysis of the ORF revealed that there was a region with very high hydrophobicity in the N-terminal sequence of the ORF. Moreover, there were two positively charged Lys residues just after the initiation amino acid, Met, of the ORF. Since this is a typical alignment of a signal sequence, the sequence of 15 amino acids, from the Met residue to the amino acid residue Just before the 16th Cys residue, was considered to be the signal sequence of ST0160.

II. Isolation of 3'-Terminal Fragment of Bst Gene a. Determination of 3'-Downstream Nucleotide Sequence of Bst Gene Two primers were synthesized for nucleotide sequence determination, as shown below, on the basis of the nucleotide sequence of the DNA insert in pBSTN:

5'-GGGGGGGAAACGAAAGAGTATTATG-3' (SEQ ID NO: 4)
(sequence 1482–1506 in Sequence ID NO: 2)

5'-ATTTTTCAAGGGGCATCCTGCTGG-3' (SEQ ID NO: 5)
(sequence 1583–1606 in SEQ. ID NO: 2)

These primers were used to analyze the nucleotide sequence of the phage DNA obtained in section I. f, that should contain the bst gene fragment. About 150 bp of the nucleotide sequence in the 3'-downstream from the HindIII recognition site of pBSTN was determined.

b. Cloning of 3'-Terminal Fragment of Bst Gene

Probe B was synthesized based no the determined sequence as follows:

5'-AAGATTTCATTTGAGGT-3' (SEQ ID NO:6)
(sequence 1665–1681 in SEQ ID NO: 2).

The phage DNA was digested with HindIII, applied to agarose gel electrophoresis, and then detected by Southern hybridization with the use of a fluorescence labeled probe B. A gene fragment of approximately 1.2 kbp hybridized intensely with probe B.

Accordingly, 5 μg of the phage DNA was digested with HindIII, separated by electrophoresis on agarose gel, and a region which contained a DNA fragment of 1.2 kbp was cut out and the DNA was extracted. The DNA was ligated into pUC19 that had been digested with HindIII and subsequently with BAP, and the resulted plasmid was used to transform E. coli MV1184. Colony hybridization of the transformants with probe B yielded 5 colonies which showed intensive hibridization.

The colonies were picked up from the agar plates, inoculated in LB-ampicillin broth, and incubated at 37° C. for 16 hr under shaking. The plasmid DNA was isolated from cells of each clone collected by centrifugation (15,000 rpm for 30 sec at 4° C.). The DNA was digested with HindIII and subjected to electrophoresis on agarose gel, which confirmed that the plasmid from any of the colonies harbored a DNA insert of an approximately 1.2 kbp fragment. All the DNA fragments of approximately 1.2 kbp hybridized intensely with probe B by Southern hybridization.

b. Analysis of C-Terminal DNA Sequence of Bst Gene Fragment

The nucleotide sequence of the DNA fragment of approximately 1.2 kbp from section a above was analyzed by ALFred DNA sequencer. The amino acid sequence deduced from the nucleotide sequence revealed a long ORF with 262 amino acids starting from a HindIII site. In the 3'-downstream of this ORF, there was a stem and loop structure which was composed of a stem of 10 bp and a loop of 7 bp.

In view of the above findings, the ORF in said fragment was supposed to represent the C-terminal sequence of the bst gene (nucleotide sequence 1634–2743 in FIGS. SEQ ID NO: 2). This plasmid was named pBSTC.

III. DNA Methyltransferase of JT0160

As shown in section I b, a DNA fragment of approximately 2.8 kbp hybridized intensely with probe A when tested by Southern hybridization of the HindIII-digested JT0160 genomic DNA. This size equaled the sum of the lengths of the gene fragments inserted in pBSTN and pBSTC, namely the length of the entire bst gene nucleotide sequence. The fact indicated that the genomic DNA was not cleaved with HindIII although the bst gene contained a HindIII-susceptible site (AAGCTT). This insusceptibility to HindIII suggested the possibility that the genomic DNA of JT0160 may be modified in the cells, such as by methylation. Analysis of the entire nucleotide sequence of the bst gene revealed that the HindIII site contained in the gene constitutes a palindrome structure G AAGCTTC, together with the flanking nucleotides. Since most restriction endonuclease sites or methylation sites comprise a palindrome, the above 8-bp sequence G AAGCTTC was considered to be the recognition site for methyltransferase of JT0160. On the other hand, the remaining HindIII sites in the ends of the bst gene had sequences AAGCTTA and AAAGCTT, respectively, which are not palindromes susceptible to methylation, and hence could be cleaved with HindIII.

Currently, a number of restriction endonucleases are known which recognize a 6 bp sequnece, and they are commonly utilized in genetic engineering. However, a recent trend demands restriction endonucleases which recognize a 8 bp sequence in order to study long genomic DNAs from the humans. In spite of such demands, Not1 is the only restriction endonuclease of a 8 bp recognition type which is commercially available. On the other hand, many bacterial species are known to possess a methyltransferase and a restriction endonuclease which recognize the same nucleotide sequence, as a defense mechanism. Since JT0160 appeared to have a DNA methyltransferase of a 8 bp recognition type, there is a possibility that this organism also has a restriction endonuclease which cleaves the sequence mentioned above. The prospect of developing the novel restriction endonuclease of a 8 bp recognition type is quite important and promising.

IV. Sialyl Motif

To date, several kinds of sialyltransferases have been purified or cloned, mainly from animal species. Sialyltransferases of animal origin possess two regions which have a significantly high homology in the amino acid sequences irrespective of their origin or species. These structures are called sialyl motives. One motif has been known to be the binding site for CMP-sialic acid which is the common sugar receptor of most sialyltransferases. No region of singificant homology was found between the estimated amino acid sequence of ST0160 and that of rat β-galactoside-α-2,3 sialyltransferase. No region of ST0160 has any significant homology with the sialyl motif sequence above, either. These facts suggest that the origin of ST1060 differs from that of animal sialyltransferases mentioned above. An analysis of this enzyme with regard to the binding site for a substrate, particularly for CMP-sialic acid will provide interesting results and such an analysis will be useful.

EXAMPLE 2

Expression of Recombinant ST0160 Protein

In this Example, we provide evidence that the long open reading frame (ORF), which was cloned as separate fragmnents in pBSTN and pBSTC, is the bst gene, ie. the gene encoding the sialyltransferase (ST0160) of Photobacterium damsela JT0160. For this purpose, the gene was inserted into an expression vector to allow the expression of the gene in E. coli and the analysis of the gene products. In addition, the obtained ST0160 production system was used to analyze the function of the region in the C-terminal sequence which is presumably responsible for binding to membranes.

I. Construction of Expression Plasmid

The bst gene was considered to be lethal to E. coli because of the fact that we could not insert the HindIII fragment of 2.8 kbp into pUC18 even though the Southern hybridization suggested the presence of a fragment of bst gene, and that the entire fragment was cloned in the two separate HindIII fragments of 1.6 kbp and 1.2 kbp. Therefore, we made an attempt to connect the two bst gene fragments that were cloned separately, under the artificially controllable tac promoter.

An expression vector employed was pAQN, a modified form of pAQI.

Figure 2:
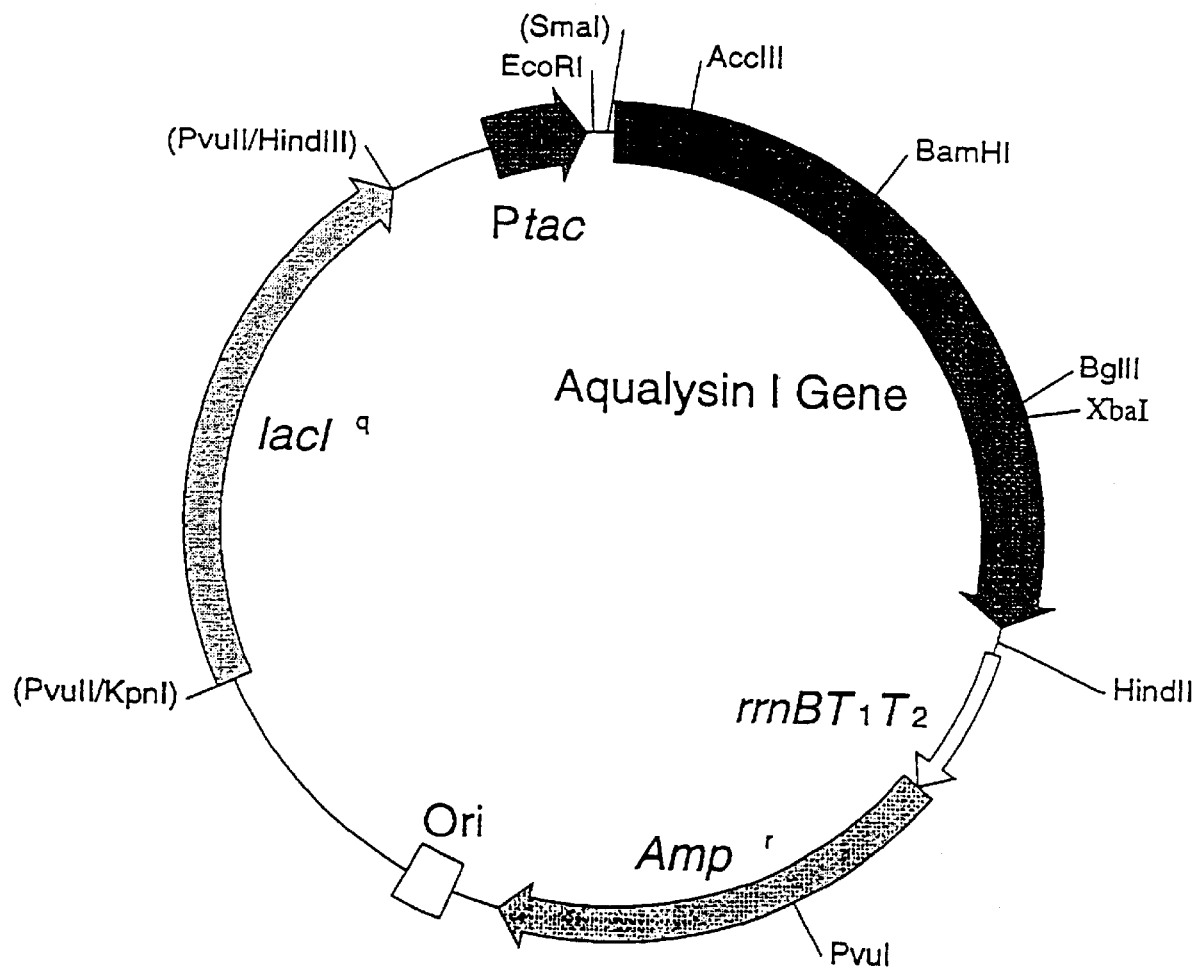
FIG. 2 illustrates the structure of pAQN.

FIG. 1 and FIG. 2 show the structure of pAQI and pAQN, respectively. These plasmids carry the gene (aqui gene), which encodes aqualysin I, between the EcoRI site just after the tac promoter and the HindIII site just before the rrnBT1T2 terminator. The aqui gene is useful for gene manipulation because it contains 10 unique restriction sites including the EcoRI and the HindIII sites in the plasmid. Moreover, the plasmid is suitable for this Experiment because it contains a lacIq which controls the tac promoter so that the tac promoter will be regulated more efficiently than in normal systems.

The method to construct pAQI is disclosed in Japanese Patent Application No. Hei2-92288, and the plasmid has been deposited as FERM BP-2305 at National Institute of Bioscience and Human Technology, Japan.

The modification of pAQI into pAQN was carried out by using Mutan-K (Takara Brewery Co.) as follows:

1. BP-2305 was grown overnight at 37° C., and pAQI was extracted from the organism by using QIAprep Spin Plasmid Kit (QIAGEN Co.).
2. pAQI was digested with XhoI and HindIII, and then ligated. (pAQIΔXH)
3. The EcoRI-XbaI fragment of the aqualysin gene was cleaved from pAQIΔXH, which was then inserted into an EcoRI-XbaI site of M13mp18. (pMBAL1)
4. The plasmid pMBAL1 was modified by way of point mutations with the following primers to create AccIII, BamHI, and BglII recognition sites within the EcoRI-XbaI segment of the aqualysin gene, and to destroy XmaIII and KpnI sites. (pMBAL1ΔXH)
   For the insertion of AccIII site (Nucleotide no. 141) (SEQ ID NO: 21)
   5'-CCTGGATGATCCGGAAGCTATCC-3' (23 mer)
   For the insertion of BamHI site (Nucleotide no. 503) (SEQ ID NO: 22) 5'-TGACACCGGGATCCGCACGA-3' (20 mer)
   For the insertion of BglII site (Nucleotide no. 966) (SEQ ID NO: 23) 5'-TAGTTGCGTAGATCTCTTCGCC-3' (22 mer)
   For the destruction of XmaIII site (Nucleotide no. 531) (SEQ ID NO: 24) 5'-AGTTCGGCGGACGGGCCCG-3' (19 mer)
   For the destruction of KpnI site (Nucleotide no. 592) (SEQ ID NO: 25) 5'-ACGGCCACGGGACCCATGTGG-3' (21 mer)
   The annealing was carried out at 65° C. for 15 min and 37° C. for 15 min.
5. The EcoR XbaI fragment was excised from pMBAL1ΔXH and inserted into plasmid AQIΔH from which the segment EcoRI baI had been deleted. (pAQN)

The construction of the plasmid pEBST, for expressing the bst gene was conducted by inserting the gene fragments from pBSTN and pBSTC into pAQN at a downstream of the tac promoter, in the orientation as described below because both fragments were HindIII fragments. Further the endogenous promoter of the bst gene was entirely removed.

Briefly, the restriction sites of pAQN aligned in the order of EcoRI, BglII, XbaI and HindIII just after the tac promoter, were changed to EcoRI, HindIII and XbaI. Next, the HpaI site (nucleotide sequence 2596–2601 in SEQ ID NO:2), in the downstream of the ORF in pBSTC, was changed to a XbaI recognition site. The ORF comprising this C-terminal sequence was inserted as a XbaI-HindIII fragment into the modified pAQN. An EcoRI site was inserted in pBSTN at an upstream of the Met codon at the N-terminus of the ORF. The ORF comprising this N-terminus was inserted as an EcoRI-HindIII fragment into pAQN, which already carried the ORF containing the C-terminal sequence, whereby to complete the construction of the expression plasmid pEBST.

Mutants which lacked the C-terminal region were constructed in a similar manner.

Figure 3:
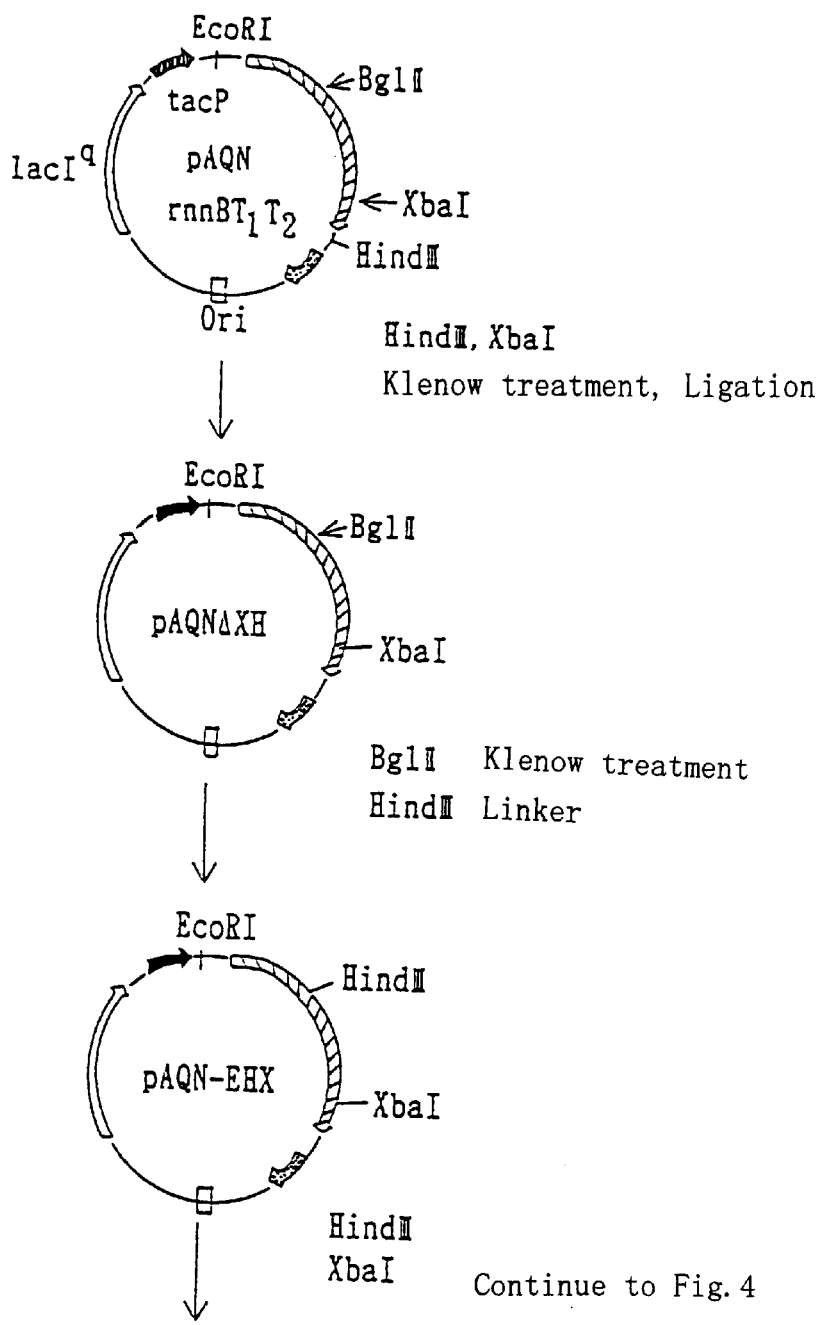
FIG. 3 illustrates the process of the construction of pAQN-EHX from pAQN.

Details are given below:
a. Materials
The following materials were used in the construction of the expression vector:
Host: *E. coli* MV1184
Plasmids: M13mp18 (Bio-Rad), M13mp19 (Bio-Rad) pUC18 (Takara Brewery), pUC19 (Takara Brewery) pBSTN, pBSTC
Expression vector: pAQN
Reagents: Wako Pure Chemicals Co.
Reagents for genetic engineering and Kits: purchased from Takara Brewery excepting Site-specific mutagenesis kit which was purchased from Bio-Rad.
Linkers:
  HindIII linker
    5'-CCAAGCTTGG-3' (SEQ ID NO:7) (Takara Brewery, 4670A)
  XbaI linker
    5'-CTCTAGAG-3' (SEQ ID NO:8) (Takara Brewery, 4693A)
Synthetic oligonucleotides:
  Primer BST01
    5'-TTATGTGAATTCGCTTAATATG-3' (SEQ ID NO:9)
  Primer BST02
    5'-TTTTTATGTGAATGTGGAATTCATGAAGAAAAT-ACTGA-3' (SEQ ID NO:10)
  Primer BST03
    5'-CAAAACAATTACTGATTAATAGTGAATTGGCG-ATGTGGCAG-3'(SEQ ID NO:11)
  Primer BST04
    5'-TGTTCTGTTCTGGGCTTAGTGATAAGATCTCTC-GATGGAAGTTGCC-3' (SEQ ID NO:12)
b. Procedures
Modification of pAQN (FIG. 3)
First, pAQN was digested with HindIII and XbaI, filled in by treatment with the Klenow fragment, and ligated again. This treatment destroyed the HindIII site whereas the XbaI site was restored (pAQNΔXH in FIG. 3). The alterations of the nucleotide sequences during the modification process are illustrated as follows:

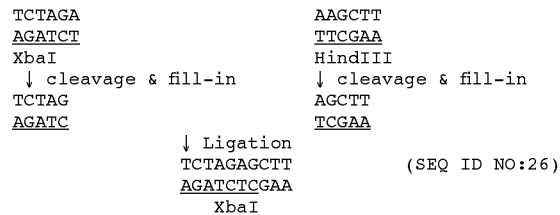

Next, pAQNΔXH was digested with BglII and filled in by a treatment with the Klenow fragment. A HindIII linker was added and the plasmid was ligated. This treatment changed the BglII site into a HindIII site (pAQN-EHX in FIG. 3).
Modification of pBSTC and Insertion into pAQN-EHX (FIG. 4)
The 1.2 kbp HindIII fragment from pBSTC, which was considered to contain a C-terminal sequence of ST0160, was inserted into the HindIII site in the cloning region of M13mp18. A colony was selected in which the 3'-terminal of the insert was oriented to the EcoRI side (ie. XbaI side) in the cloning region (pMBSTC in FIG. 4).
Then, pMBSTC was cleaved with HpaI, filled in by a treatment with the Klenow fragment, a XbaI linker was added, and the plasmid was ligated, whereby the HpaI site was changed to a XbaI site (pMBSTC-HX in FIG. 4).

Figure 4:
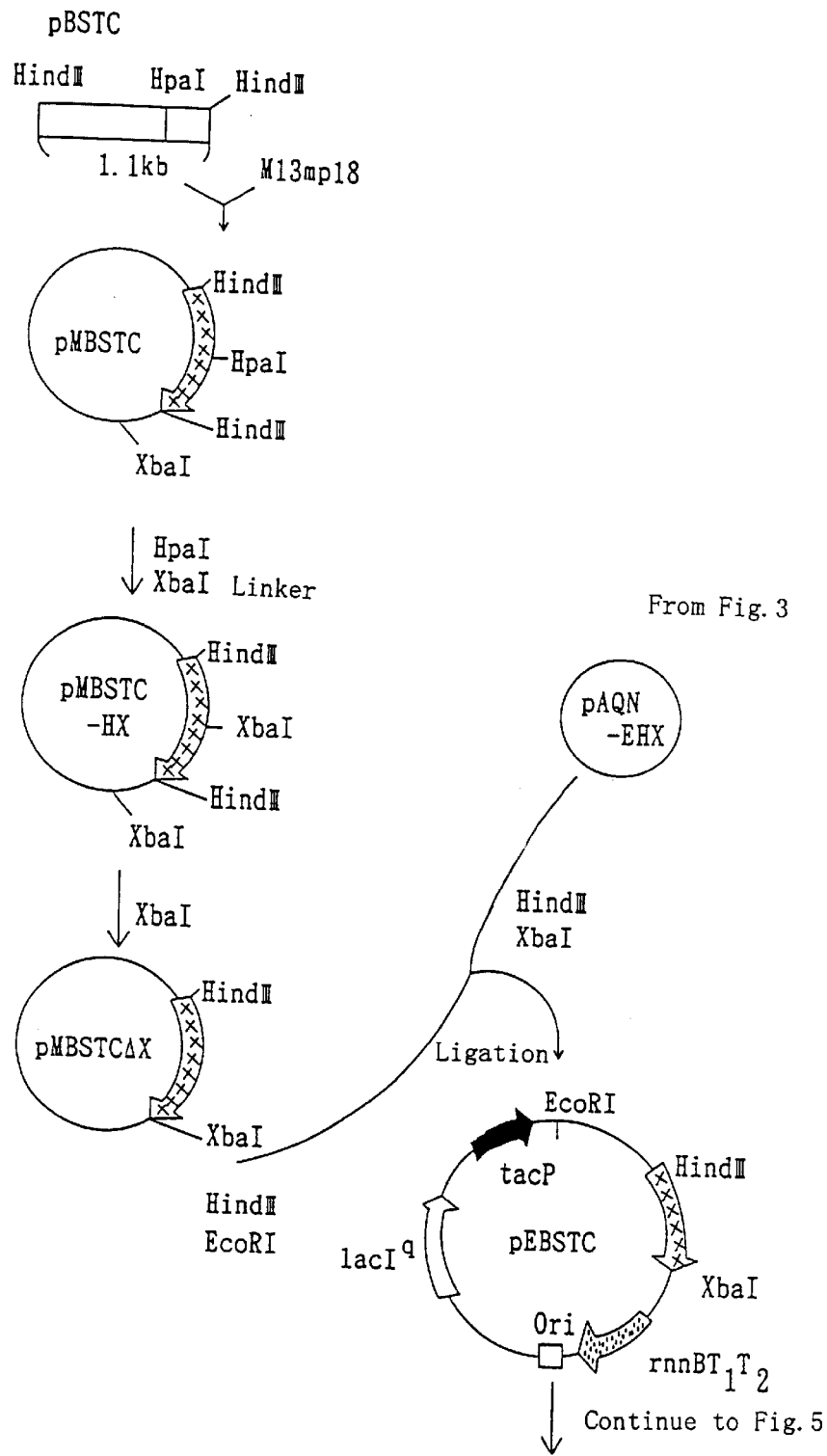
FIG. 4 illustrates the process of the construction of pEBSTC from pBSTC.

The plasmid pMBSTC-HX was digested with XbaI and ligated without further treatment, which resulted in deletion of the excess XbaI fragment (that contained a HindIII site)(pMBSTCΔX in FIG. 4).

The HindIII-XbaI fragment, from pMBSTCΔX, was inserted into the HindIII-XbaI site of pAQN-EHX, to generate pEBSTC.

Construction of Modified ST0160 Lacking the Membrane-Binding Region

We also constructed a modified form of ST0160 lacking the potential membrane binding region (abbreviated as M, hereafter) and the region which is highly homologous to phoU (abbreviated as P, hereafter), in order to clarify their functions and effects on the expression.

The procedure for this modification was as follows: The plasmid pMBSTCΔX (FIG. 4) was subjected to site-specific mutagenesis at the codons encoding the 539 th amino acid leucine in the ORF sequence (by using primer BST03) and the 498th aspartic acid (by using primer BNST04), and these codons were respectively converted to termination codons. Plasmids so constructed were pMBSTRCΔC137 and pMBSTCΔC178, respectively. In said mutagenesis, 3 different termination codons were inserted to ensure the stoppage of translation, and further, a new restriction site was inserted to provide convenient means for confirming the mutation (PshBI for pMBSTCΔC137 and BglII for pMBSTCΔC178, respectively).

From pMBSTCΔC137 and pMBSTCΔC178 their HindIII-XbaI fragment was removed and the respective fragment was inserted into the HindIII-XbaI site of pAQN-EHX as described in the construction of pMBSTCΔX, whereby pEBST (pEBSTCΔC137 and pEBSTCΔC178, respectively) were constructed.

Figure 5:
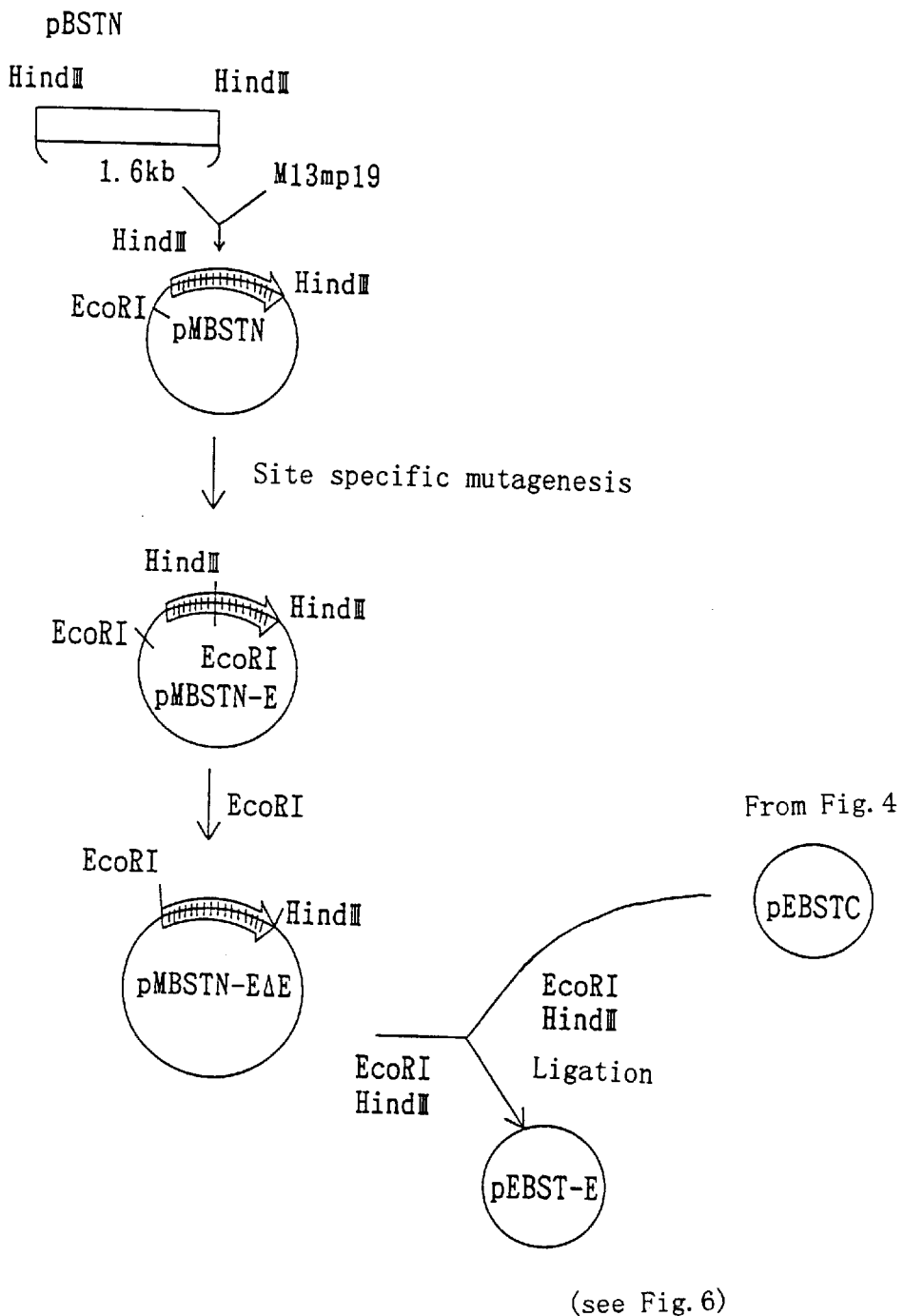
FIG. 5 illustrates the process of the construction of pEBST from pBSTN.

Construction of Expression Vector by Modification and Insertion of pBSTN into pEBSTC (FIG. 5)

We excised the 1.6 kbp HindIII fragment, which was considered to comprise a N-terminal sequence of ST0160, from pBSTN as constructed in section I h of Example 1, and inserted it into the HindIII site of the M13mp19 cloning region. A clone was selected which contained the insert in the orientation that the N-terminal was oriented to EcoRI in the cloning region (pMBSTN in FIG. 5).

Next, an EcoRI site was inserted in pBSTN, by site-specific mutagenesis, at an upstream of the ORF starting point. Two recombinant plasmids were constructed: One was plasmid pMBSTN-E0 that had no nucleotides between the EcoRI site and the methionine codon ATG (by using primer BST02), and the other was plasmid pMBSTN-E7 that had 7 nucleotides between them (by using primer BST01). When pMBSTN-E0 was inserted into pAQN, the distance between the SD sequence and the ATG was 9 bp whereas pMBSTN-E7 afforded 16 bp by the insertion. It was expected that the distance of 9 bases between the SD sequence and the ATG afforded by pMBSTN-E0 would achieve the most efficient expression due to this distance. On the other hand, the greater distance between the SD sequence and the ATG was created in pMBSTN-E7 in the attempt to construct an expression system where the expression is reduced in view of the possibility that the bst gene is lethal to E. coli, as described above.

Plasmids pMBSTN-E0 and pMBSTN-E7 were respectively digested with EcoRI and ligated without any further treatment, to remove the excessive EcoRI fragment (including a HindIII site)(pMBSTN-E0ΔE and pMBSTN-E7ΔE, in FIG. 5).

Figure 6:
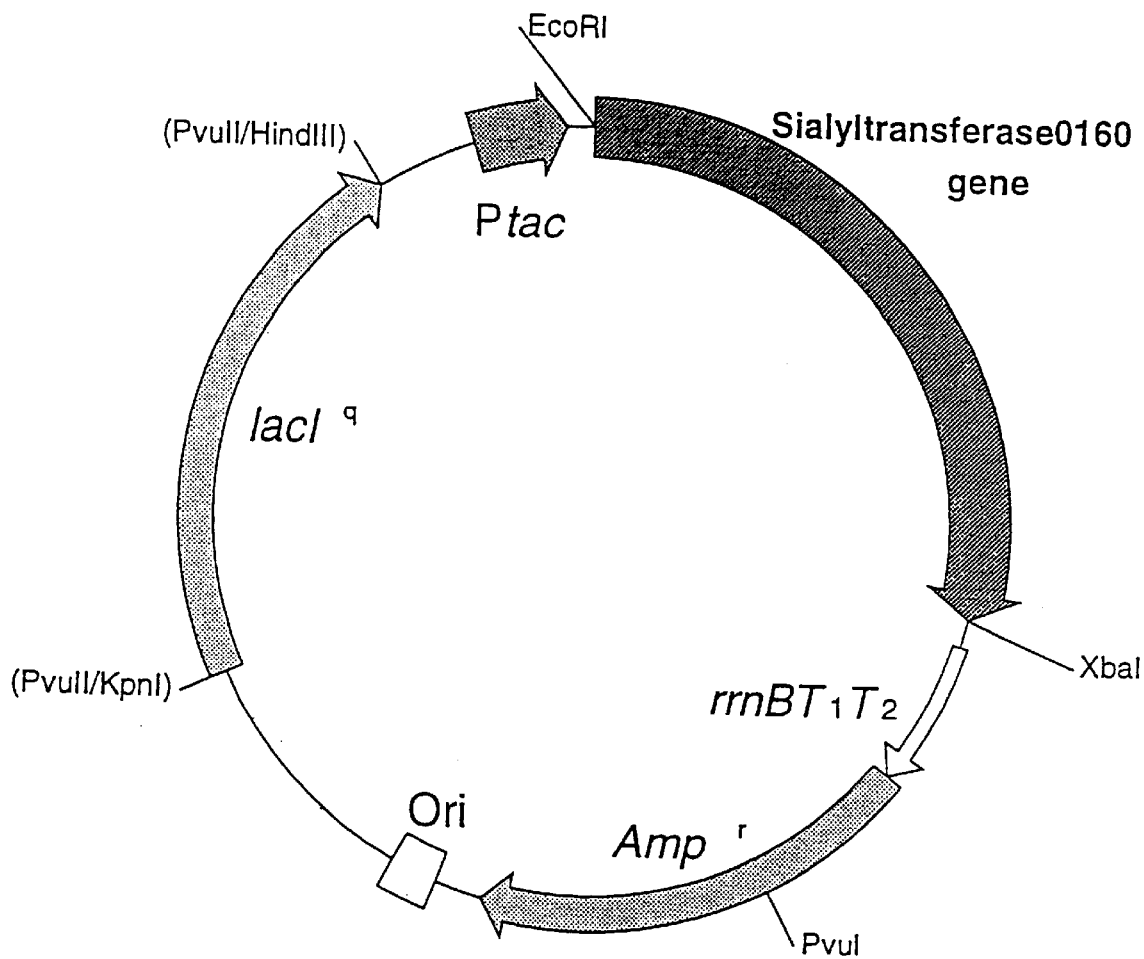
FIG. 6 illustrates the structure of the expression vector pEBST.

The respective EcoRI fragment, excised from pMBSTN-E0ΔE and pMBSTN-E7ΔE, was inserted into the EcoRI-HindIII site of pEBSTC, to generate expression vectors of pEBST (FIG. 6).

A similar insertion was made to pEBSTCΔC137 and pEBSTCΔC178. In total, 6 ST1060 expression vectors were constructed as shown in Table 2.

TABLE 2

| |
|---|
| pEBST-E0 = pBSTN-E0ΔE + pEBSTC = A2 Series |
| pEBST-E7 = pBSTN-E7ΔE + pEBSTC = A1 Series |
| pEBST-E0AM = pBSTN-E0ΔE + pBSTNCΔvC137 = B2 Series |
| pEBST-E7ΔM = pBSTN-E7ΔE + pBSTNCΔC137 = B1 Series |
| pEBST-E0ΔP = pBSTN-E0ΔE + pBSTNCΔC178 = C2 Series |
| pEBST-E7ΔP = pBSTN-E7ΔE + pBSTNCΔC178 = 12 Series |

II. Example for expression (1) Transformation and preservation of bacterial strains Each of the six expression vectors (10 μl) shown in Table 2, was added to competent cells of E. coli MV1184 (100 μl) that were thawed on ice from the stock stored at −80° C. The mixture was placed on ice for 30 min, heated at 42° C. for 1 min, and again placed on ice for 3 min. To this, 900 μl of prewarmed LB broth was added and the mixture was shaken at 37° C. for 1 hr. Then, aliquots of the mixture were spread on agar plates containing LB, ampicillin, IPTG, and X-Gal. The agar plates were incubated at 37° C. for 16 hr.

(2) Cultivation

Transformants (6 types) were grown in LB broth containing ampicillin and IPTG under shaking at 150 rpm at 30° C., and their growth and sialyltransferase activity were measured. The inoculum size to the medium was 0.5% of the cells that were prepared in section (1) and stored in glycerol. The growth medium contained 100 mg/l ampicillin and 0.02 mM IPTG. The growth was monitored by sampling an aliquot, at time intervals, to measure its turbidity at 660 nm.

Figure 9:
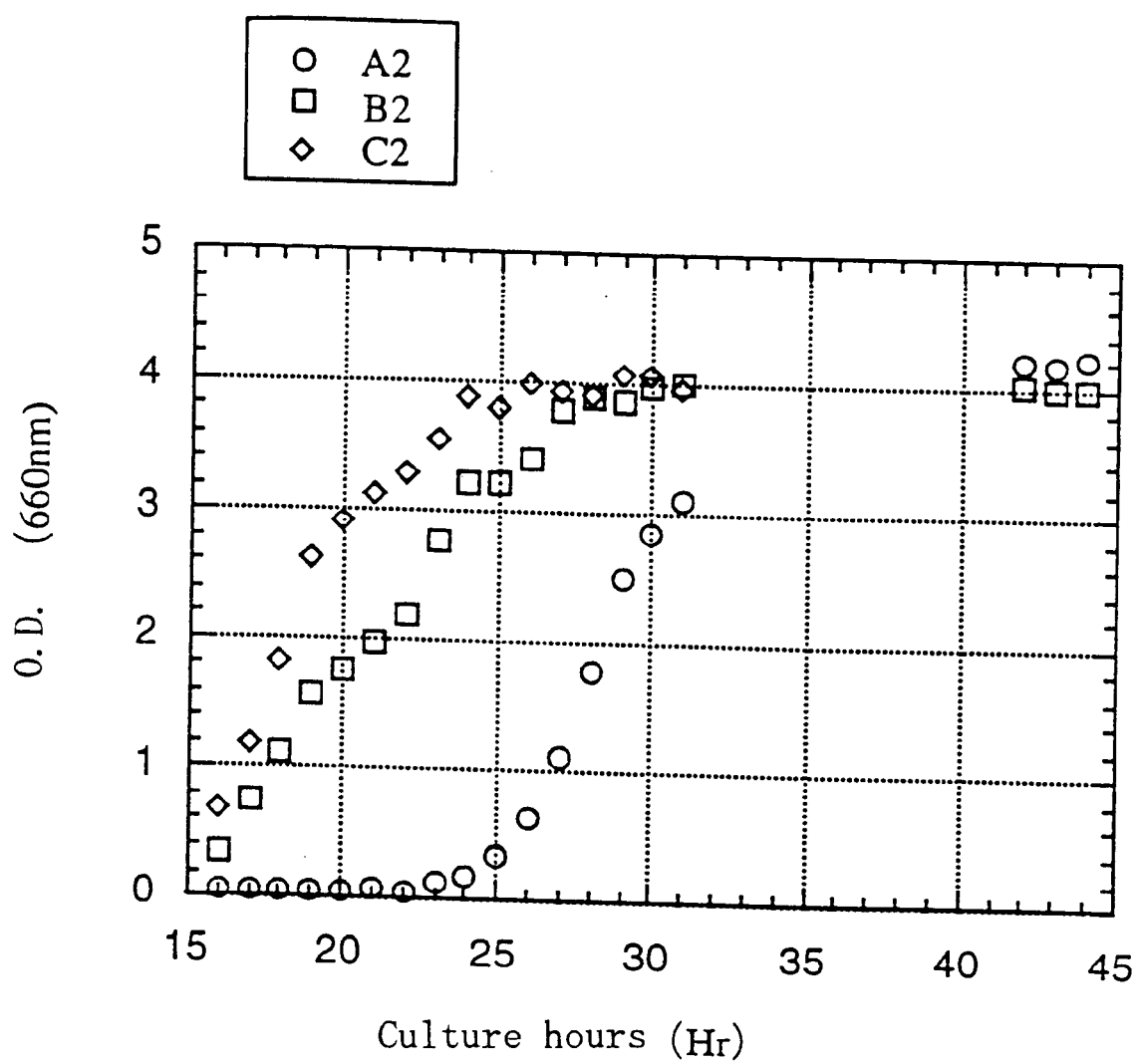
FIG. 9 shows the growth of *E. coli* MV1184 transformant strains (A2, B2 and C2) containing an expression vector of the present invention.

The results showed that each of the transformants of E. coli MV1184 harboring the expression vectors, A, B and C series started growing after a long lag time. The growth rates of the transformants (A2, B2, and C2) were compared as C series>B series>A series, as shown in FIG. 9.

A crude enzyme preparation was prepared by collecting cells under centrifugation, resuspending them in 20 mM cacodylate buffer (pH 5.0) containing 0.2% Triton X-100, and disrupting them in a sonicator. As shown in Table 3, the level of enzyme production was also in the order of C>B>A.

Sialyltransferase activity was measured in terms of the amount of [4,5,6,7,8,9-$^{14}$C]-NeuAc transferred to the acceptor substrate lactose from the donor substrate CMP-[4,5,6,7,8,9-$^{14}$C]-NeuAc. The standard reaction mixture consisted of an enzyme sample in 20 mM cacodylate-sodium buffer (pH 5.0) containing 70 nmol of CMP-[4,5,6,7,8,9-$^{14}$C]-NeuAc (642 cpm/nmol), 1.25 μmol of lactose and 0.02% Triton X-100 in a total volume of 25 μl. The enzyme reaction was conducted at 30° C. for 3 min, in duplicate for all the measurements. After this period, the reaction mixture was diluted to 2 ml by addition of 5 mM sodium-phosphate buffer (pH 6.8) and applied onto a Dowex 1 x 8 column (phosphate form, 0.5×2 cm). The eluate (2 ml) was collected directly in a scintillation vial and measured for radioactivity. The radioactivity of [4,5,6,7,8, 9-$^{14}$C]-NeuAc in the eluate was measured with a liquid scintillation counter to calculate the amount of the [4,5,6,7,8,9-$^{14}$C]-NeuAc that was transferred to the acceptor substrate. One unit (U) of the enzyme activity was defined by 1 μmol of sialic acid transferred to lactose in 1 min under the above conditions.

TABLE 3

| | |
|---|---|
| A1 series | 43 units/L |
| A2 series | 66 units/L |
| B1 series | 74 units/L |
| B2 series | 112 units/L |
| C1 series | 91 units/L |
| C2 series | 240 units/L |

(3) Characterization of the enzymatic reaction products

The crude enzyme extract, prepared as described in section (2) above, was partially purified by column chromatography with an ion-exchange column (Q-Sepharose, Pharmacia) and then with hydroxyapatite (Kouken Co.). The reaction with this enzyme preparation was performed with pyridylamino-lactose as the sugar acceptor substrate and CMP-NeuAc as the sugar donor substrate, at 30° C. for 6 hr. After reaction, the enzyme was inactivated by heating at 100° C. for 2 min, and the reaction product was analyzed by HPLC.

The HPLC analysis was carried out by injecting 10 μl of the reaction mixture, after the enzyme was inactivated, into PALPAK type R column (Takara Brewery Co.) that was provided on Shimazu LC-10 HPL system (Shimazu Co.) and equilibrated with a solution of 100 mM acetic acid-triethylamine (pH 5.0) containing 0.15% n-butanol. For elution of pyridylamino-sugar chains, solution A (100 mM acetic acid-triethylamine, pH 5.0) and solution B (100 mM acetic acid-triethylamine, pH 5.0, that contained 0.5% n-butanol) were used as a linear gradient that started from 30% B up to 100% B (0–35 min) and then 100% B alone (35–50 min), with an elution rate of 1 ml/min and at a column temperature of 40° C. Pyridylamino-sugar chains were detected by fluorescence (excitation at 320 nm and emission at 400 nm) of the eluate.

Figure 10:
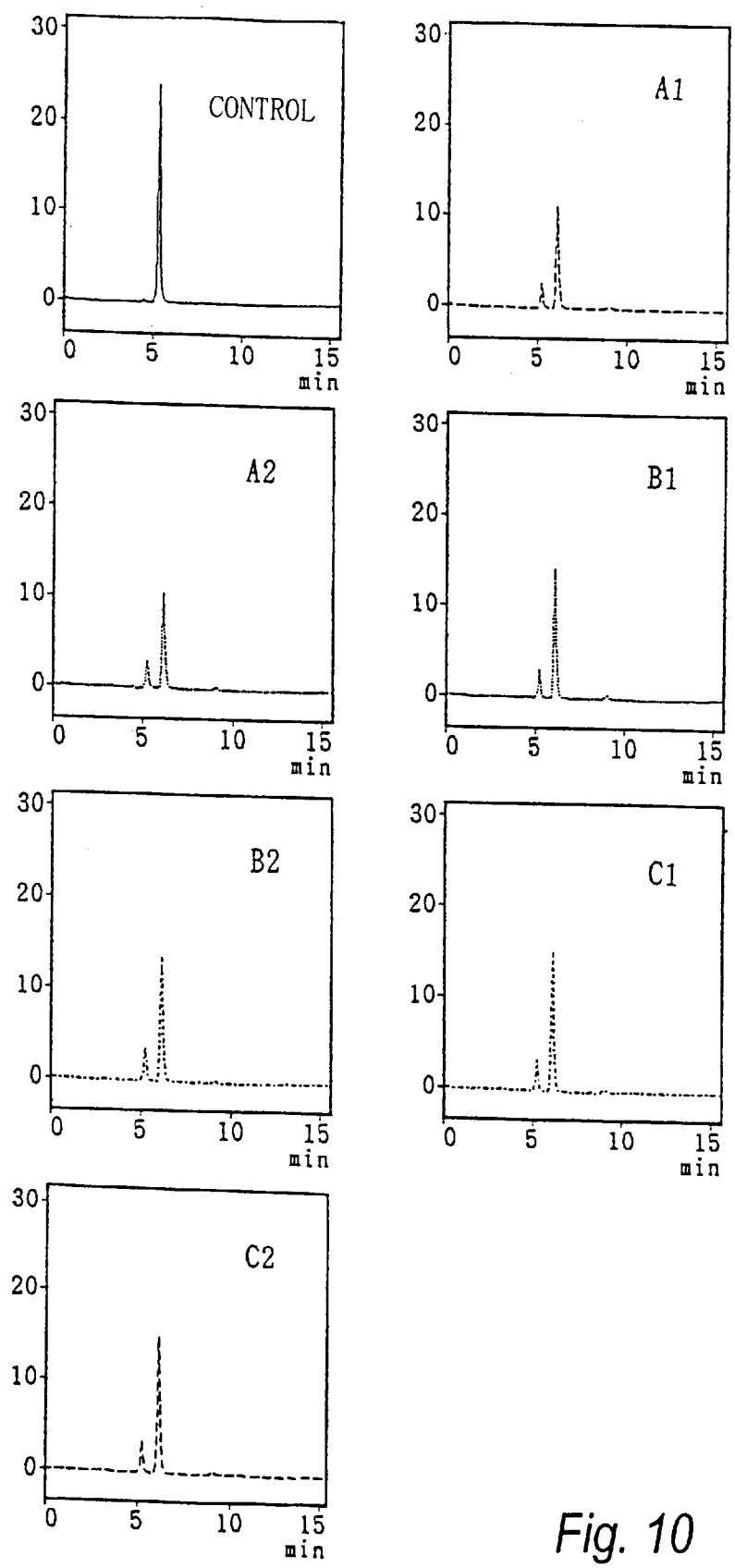
FIG. 10 shows the retention time of the enzymatic reaction products of the crude enzymes which acted on CMP-NeuAc employed as a sugar donor substrate. The figure shows that the crude enzymes obtained from the 6 transformants in Example 2 II(2) have the same activity as that of ST0160.

The results in FIG. 10 show that the reaction products by any of the crude enzyme preparations gave a peak of the retention time which was the same as that of the reaction product of pure ST0160 enzyme, indicating that all 6 crude enzyme preparations transferred sialic acid to the galactose moiety at the position 6, to form an α2,6-linkage.

(4) Solubilized enzyme

Generally speaking, any protein in supernatant solution from a centrifugation at 100,000×g for 1 hr is defined as a solublized protein. Therefore, the C2 series organism was grown in LB-penicillin-IPTG broth under shaking at 150 rpm and at 30° C., and a crude enzyme extract was prepared from the cells collected by centrifugation by way of sonic disruption in 20 mM cacodylate buffer (pH 5.0). The cell suspension disrupted by sonic treatment was centrifuged at 100,000×g for 1 hr, at 4° C., and the supernatant was tested for sialyltransferase activity. The enzyme activity in the supernatant was about 50% (120 units/L) of the total enzyme activity produced in section (2) above. A similar experiment with clones A1 and A2 series did not give any substantial enzyme activity in the supernatant solution of 100,000×g for 1 hr unless a detergent was added in the extraction buffer. Consequently, it was determined that the C-terminal portion of the gene encoding this enzyme is the region which is involved in the binding to membranes, and that it is possible to produce a soluble type of sialyltransferase artificially by deleting said portion.

(5) Sialyltransferase activity in the supernatant medium after the growth of C2 transformant A transfromant strain of C2 series was grown in LB-ampicillin-IPTG medium under shaking at 150 rpm at 30° C. When reading at $OD_{600}$ reached 2.8, 970 ml portion of the growth medium was removed from the culture and sialyltransferase activity was measured.

Sialyltransferase activity was measured by the amount of [4,5,6,7,8,9-$^{14}$C]-NeuAc that was transferred to the acceptor substrate lactose from the donor substrate CMP-[4,5,6,7,8, 9-$^{14}$C]-NeuAc. The standard reaction mixture consisted of an enzyme sample in 20 mM cacodylate-sodium buffer (pH 5.0) containing 70 nmol of CMP-[4,5,6,7,8,9-$^{14}$C]-NeuAc (642 cpm/nmol), 1.25 μmol of lactose and 0.02% Triton X-100 in a total volume of 25 μl. The enzyme reaction was conducted at 30° C. for 3 min, in duplicate for all the measurements. After reaction, the reaction mixture was diluted to 2 ml by addition of 5 mM sodium-phosphate buffer (pH 6.8) and applied to a Dowex 1×8 column (phosphate form, 0.5×2 cm). Eluate (2 ml) was directly collected in a scintillation vial and measured for radioactivity. The radioactivity of [4,5,6,7,8,9-$^{14}$C]- NeuAc in the eluate was measured with a liquid scintillation counter to calculate the amount of the [4,5,6,7,8,9-$^{14}$C]-NeuAc that was transferred to the acceptor substrate. One unit (U) of the enzyme activity was defined by 1 μmol of sialic acid transferred to lactose in 1 min under the above conditions.

Sialyltransferase activity was 12.98 U/1 was obserbed.

What is claimed is:

1. An isolated and purified nucleic acid encoding a protein having the amino acid sequence comprising the amino acid residues 16–498 of SEQ ID NO:1.

2. An isolated and purified nucleic acid selected from the group consisting of the following (a) or (b):
   (a) a DNA comprising the nucleotide sequence 46–1494 of SEQ ID NO:2, or
   (b) a DNA comprising a nucleotide sequence which is capable of hybridizing to the nucleotide sequence 46–1494 of SEQ ID NO:2 under mild stringency wherein said DNA encodes a protein having β-galactoside-α2,6-sialyltransferase activity.

3. An isolated and purified nucleic acid according to claim 1 wherein the nucleic acid further comprises a nucleotide sequence which encodes the amino acid sequence comprising the amino acid residues 499-X of SEQ ID NO:1, wherein X represents an integer from 500–675 inclusive.

4. An isolated and purified nucleic acid according to claim 1 wherein the nucleic acid further comprises a nucleotide sequence which encodes the amino acid sequence comprising the amino acid residues 499-X of SEQ ID NO:1, wherein X represents an integer from 500–675 inclusive.

5. An expression vector which comprises a nucleic acid of claim 1.

6. An expression vector which comprises a nucleic acid of claim 2.

7. An expression vector which comprises a nucleic acid of claim 3.

8. An expression vector which comprises a nucleic acid of claim 4.

9. An expression vector according to any of claims 5–8, which comprises a DNA that encodes a signal peptide selected from the group consisting of the following (A) or (B):
  (A) a DNA encoding the amino acid sequence comprising the amino acid residues 1–15 of SEQ ID NO:1, or
  (B) a DNA comprising a nucleotide sequence which is capable of hybridizing to the DNA encoding the amino acid sequence comprising the amino acid residues 1–15 of SEQ ID NO:1 under mild stringency, wherein said DNA encodes a peptide maintaining peptide activity.

10. An expression vector according to any of claims 5–8, which comprises a DNA that encodes a signal peptide derived from the host to be transformed.

11. An expression vector according to claim 9, which comprises a DNA that encodes a signal peptide derived from the host to be transformed.

12. A process for producing a recombinant β-galactoside-α2,6-sialyltransferase protein which comprises growing cells of a host organism transformed with a vector of any of claims 5–8 under conditions which allow the cells to express β-galactoside-α2,6-sialyltransferase, and recovering the β-galactoside-α2,6-sialyltransferase protein from the culture.

13. A process for producing a recombinant β-galactoside-α2,6-sialyltransferase protein which comprises growing cells of a host organism transformed with a vector of claim 9 under conditions which allow the cells to express β-galactoside-α2,6-sialyltransferase, and recovering the β-galactoside-α2,6-sialyltransferase protein from the culture.

14. A process for producing a recombinant β-galactoside-α2,6-sialyltransferase protein which comprises growing cells of a host organism transformed with a vector of claim 10 under conditions which allow the cells to express β-galactoside-α2,6-sialyltransferase, and recovering the β-galactoside-α2,6-sialyltransferase protein from the culture.

15. A process for producing a recombinant β-galactoside-α2,6-sialyltransferase protein which comprises growing cells of a host organism transformed with a vector of claim 11 under conditions which allow the cells to express β-galactoside-α2,6-sialyltransferase, and recovering the β-galactoside-α2,6-sialyltransferase protein from the culture.

16. An isolated and purified nucleic acid selected from the group consisting of the following (a) or (b):
  (a) a DNA comprising the nucleotide sequence 46–1494 of SEQ ID NO:2, or
  (b) a DNA comprising a nucleotide sequence which is capable of hybridizing to the nucleotide sequence 46–1494 of SEQ ID NO:2 under mild stringency wherein said DNA encodes a protein having 4 β-galactoside-α2,6-sialyltransferase activity, wherein the protein has at least 50% homology to the protein encoded by the DNA of (a).

* * * * *

SEQUENCE LISTING

<160> NUMBER OF SEQ ID NOS: 26

<210> SEQ ID NO 1
<211> LENGTH: 675
<212> TYPE: PRT
<213> ORGANISM: Photobacterium damsela

<400> SEQUENCE: 1

Met Lys Lys Ile Leu Thr Val Leu Ser Ile Phe Ile Leu Ser Ala Cys
 1               5                  10                  15

Asn Ser Asp Asn Thr Ser Leu Lys Glu Thr Val Ser Ser Asn Ser Ala
            20                  25                  30

Asp Val Val Glu Thr Glu Thr Tyr Gln Leu Thr Pro Ile Asp Ala Pro
        35                  40                  45

Ser Ser Phe Leu Ser His Ser Trp Glu Gln Thr Cys Gly Thr Pro Ile

-continued

```
                50                  55                  60
Leu Asn Glu Ser Asp Lys Gln Ala Ile Ser Phe Asp Phe Val Ala Pro
 65                  70                  75                  80

Glu Leu Lys Gln Asp Glu Lys Tyr Cys Phe Thr Phe Lys Gly Ile Thr
                 85                  90                  95

Gly Asp His Arg Tyr Ile Thr Asn Thr Thr Leu Thr Val Val Ala Pro
                100                 105                 110

Thr Leu Glu Val Tyr Ile Asp His Ala Ser Leu Pro Ser Leu Gln Gln
                115                 120                 125

Leu Ile His Ile Ile Gln Ala Lys Asp Glu Tyr Pro Ser Asn Gln Arg
                130                 135                 140

Phe Val Ser Trp Lys Arg Val Thr Val Asp Ala Asp Asn Ala Asn Lys
145                 150                 155                 160

Leu Asn Ile His Thr Tyr Pro Leu Lys Gly Asn Asn Thr Ser Pro Glu
                165                 170                 175

Met Val Ala Ala Ile Asp Glu Tyr Ala Gln Ser Lys Asn Arg Leu Asn
                180                 185                 190

Ile Glu Phe Tyr Thr Asn Thr Ala His Val Phe Asn Asn Leu Pro Pro
                195                 200                 205

Ile Ile Gln Pro Leu Tyr Asn Asn Glu Lys Val Lys Ile Ser His Ile
                210                 215                 220

Ser Leu Tyr Asp Asp Gly Ser Ser Glu Tyr Val Ser Leu Tyr Gln Trp
225                 230                 235                 240

Lys Asp Thr Pro Asn Lys Ile Glu Thr Leu Glu Gly Glu Val Ser Leu
                245                 250                 255

Leu Ala Asn Tyr Leu Ala Gly Thr Ser Pro Asp Ala Pro Lys Gly Met
                260                 265                 270

Gly Asn Arg Tyr Asn Trp His Lys Leu Tyr Asp Thr Asp Tyr Tyr Phe
                275                 280                 285

Leu Arg Glu Asp Tyr Leu Asp Val Glu Ala Asn Leu His Asp Leu Arg
290                 295                 300

Asp Tyr Leu Gly Ser Ser Ala Lys Gln Met Pro Trp Asp Glu Phe Ala
305                 310                 315                 320

Lys Leu Ser Asp Ser Gln Gln Thr Leu Phe Leu Asp Ile Val Gly Phe
                325                 330                 335

Asp Lys Glu Gln Leu Gln Gln Gln Tyr Ser Gln Ser Pro Leu Pro Asn
                340                 345                 350

Phe Ile Phe Thr Gly Thr Thr Thr Trp Ala Gly Gly Glu Thr Lys Glu
                355                 360                 365

Tyr Tyr Ala Gln Gln Gln Val Asn Val Ile Asn Asn Ala Ile Asn Glu
                370                 375                 380

Thr Ser Pro Tyr Tyr Leu Gly Lys Asp Tyr Asp Leu Phe Phe Lys Gly
385                 390                 395                 400

His Pro Ala Gly Gly Val Ile Asn Asp Ile Ile Leu Gly Ser Phe Pro
                405                 410                 415

Asp Met Ile Asn Ile Pro Ala Lys Ile Ser Phe Glu Val Leu Met Met
                420                 425                 430

Thr Asp Met Leu Pro Asp Thr Val Ala Gly Ile Ala Ser Ser Leu Tyr
                435                 440                 445

Phe Thr Ile Pro Ala Asp Lys Val Asn Phe Ile Val Phe Thr Ser Ser
                450                 455                 460

Asp Thr Ile Thr Asp Arg Glu Glu Ala Leu Lys Ser Pro Leu Val Gln
465                 470                 475                 480
```

```
Val Met Leu Thr Leu Gly Ile Val Lys Glu Lys Asp Val Leu Phe Trp
            485                 490                 495

Ala Asp His Lys Val Asn Ser Met Glu Val Ala Ile Asp Glu Ala Cys
        500                 505                 510

Thr Arg Ile Ile Ala Lys Arg Gln Pro Thr Ala Ser Asp Leu Arg Leu
    515                 520                 525

Val Ile Ala Ile Ile Lys Thr Ile Thr Asp Leu Glu Arg Ile Gly Asp
530                 535                 540

Val Ala Glu Ser Ile Ala Lys Val Ala Leu Glu Ser Phe Ser Asn Lys
545                 550                 555                 560

Gln Tyr Asn Leu Leu Val Ser Leu Glu Ser Leu Gly Gln His Thr Val
                565                 570                 575

Arg Met Leu His Glu Val Leu Asp Ala Phe Ala Arg Met Asp Val Lys
            580                 585                 590

Ala Ala Ile Glu Val Tyr Gln Glu Asp Asp Arg Ile Asp Gln Glu Tyr
        595                 600                 605

Glu Ser Ile Val Arg Gln Leu Met Ala His Met Met Glu Asp Pro Ser
    610                 615                 620

Ser Ile Pro Asn Val Met Lys Val Met Trp Ala Ala Arg Ser Ile Glu
625                 630                 635                 640

Arg Val Gly Asp Arg Cys Gln Asn Ile Cys Glu Tyr Ile Ile Tyr Phe
                645                 650                 655

Val Lys Gly Lys Asp Val Arg His Thr Lys Pro Asp Asp Phe Gly Thr
            660                 665                 670

Met Leu Asp
        675

<210> SEQ ID NO 2
<211> LENGTH: 2743
<212> TYPE: DNA
<213> ORGANISM: Photobacterium damsela
<220> FEATURE:
<221> NAME/KEY: CDS
<222> LOCATION: (396)..(2420)

<400> SEQUENCE: 2
aagcttatct tgaaatgaat gataaggaag gggcgattga attacttgaa gaggtaacgg     60
caaaagcgga tggggctgta aaagcggaag ctgaggaagt tattgaataa ctaattttc    120 aaatgttctg ttttaaggcg taaacgattg agtctcttaa agcgtactat gtcatcataa    180
ggctggtgtg gcatagtacg cacttttaat gatcttcatt atttattact tattggtatg    240
acagtttgta aataataatt tttcaattga tattttatg ctggtattga acctgaaatc    300
aaatgagata tatctcacaa aaagcaaatg taaacatcat cttaaataga tgaggcaata    360
tactactaag aatttttat gtgaatgtgc ttaat atg aag aaa ata ctg aca        413
                                      Met Lys Lys Ile Leu Thr
                                        1               5 gtt cta tct att ttt att ctt tca gcg tgt aat agt gac aat acc agc      461
Val Leu Ser Ile Phe Ile Leu Ser Ala Cys Asn Ser Asp Asn Thr Ser
             10                  15                  20 ttg aaa gaa acg gta agc tct aat tct gca gat gta gta gaa aca gaa      509
Leu Lys Glu Thr Val Ser Ser Asn Ser Ala Asp Val Val Glu Thr Glu
         25                  30                  35 act tac caa ctg aca ccg att gat gct cct agc tct ttt tta tct cat      557
Thr Tyr Gln Leu Thr Pro Ile Asp Ala Pro Ser Ser Phe Leu Ser His
     40                  45                  50
```

-continued

| | | |
|---|---|---|
| tct tgg gag caa aca tgt ggc aca cct atc ttg aat gaa agt gac aag<br>Ser Trp Glu Gln Thr Cys Gly Thr Pro Ile Leu Asn Glu Ser Asp Lys<br>55                            60                       65                   70 | 605 |
| caa gcg ata tct ttt gat ttt gtt gct cca gag tta aag caa gat gaa<br>Gln Ala Ile Ser Phe Asp Phe Val Ala Pro Glu Leu Lys Gln Asp Glu<br>                    75                       80                       85 | 653 |
| aag tat tgt ttt act ttt aaa ggt att aca ggc gat cat agg tat atc<br>Lys Tyr Cys Phe Thr Phe Lys Gly Ile Thr Gly Asp His Arg Tyr Ile<br>                90                        95                      100 | 701 |
| aca aat aca aca tta act gtt gtt gca cct acg cta gaa gtt tac atc<br>Thr Asn Thr Thr Leu Thr Val Val Ala Pro Thr Leu Glu Val Tyr Ile<br>                105                     110                 115 | 749 |
| gat cat gca tcc tta cca tcg cta cag cag ctt atc cac att att caa<br>Asp His Ala Ser Leu Pro Ser Leu Gln Gln Leu Ile His Ile Ile Gln<br>120                           125                     130 | 797 |
| gca aaa gat gaa tac cca agt aat caa cgt ttt gtc tct tgg aag cgt<br>Ala Lys Asp Glu Tyr Pro Ser Asn Gln Arg Phe Val Ser Trp Lys Arg<br>135                           140                     145                 150 | 845 |
| gta act gtt gat gct gat aat gcc aat aag tta aac att cat act tat<br>Val Thr Val Asp Ala Asp Asn Ala Asn Lys Leu Asn Ile His Thr Tyr<br>                   155                     160                     165 | 893 |
| cca tta aaa ggc aat aat acc tca cca gaa atg gtg gca gcg att gat<br>Pro Leu Lys Gly Asn Asn Thr Ser Pro Glu Met Val Ala Ala Ile Asp<br>                170                     175                 180 | 941 |
| gag tat gct cag agc aaa aat cga ttg aat ata gag ttc tat aca aat<br>Glu Tyr Ala Gln Ser Lys Asn Arg Leu Asn Ile Glu Phe Tyr Thr Asn<br>                   185                     190                 195 | 989 |
| aca gct cat gtt ttt aat aat tta cca cct att att caa cct tta tat<br>Thr Ala His Val Phe Asn Asn Leu Pro Pro Ile Ile Gln Pro Leu Tyr<br>200                           205                     210 | 1037 |
| aat aac gag aag gtg aaa att tct cat att agt ttg tat gat gat ggt<br>Asn Asn Glu Lys Val Lys Ile Ser His Ile Ser Leu Tyr Asp Asp Gly<br>215                           220                     225                 230 | 1085 |
| tct tct gaa tat gta agt tta tat caa tgg aaa gat aca cca aat aag<br>Ser Ser Glu Tyr Val Ser Leu Tyr Gln Trp Lys Asp Thr Pro Asn Lys<br>                   235                     240                 245 | 1133 |
| ata gaa aca tta gaa ggt gaa gta tcg ctt ctt gct aat tat tta gca<br>Ile Glu Thr Leu Glu Gly Glu Val Ser Leu Leu Ala Asn Tyr Leu Ala<br>                250                     255                 260 | 1181 |
| gga aca tct ccg gat gca cca aaa gga atg gga aat cgt tat aac tgg<br>Gly Thr Ser Pro Asp Ala Pro Lys Gly Met Gly Asn Arg Tyr Asn Trp<br>                   265                     270                 275 | 1229 |
| cat aaa tta tat gac act gat tat tac ttt ttg cgc gaa gat tac ctt<br>His Lys Leu Tyr Asp Thr Asp Tyr Tyr Phe Leu Arg Glu Asp Tyr Leu<br>280                           285                     290 | 1277 |
| gac gtt gaa gca aac cta cat gat tta cgt gat tat tta ggc tct tcc<br>Asp Val Glu Ala Asn Leu His Asp Leu Arg Asp Tyr Leu Gly Ser Ser<br>295                           300                     305                 310 | 1325 |
| gca aag caa atg cca tgg gat gaa ttt gct aaa tta tct gat tct cag<br>Ala Lys Gln Met Pro Trp Asp Glu Phe Ala Lys Leu Ser Asp Ser Gln<br>                   315                     320                 325 | 1373 |
| caa aca cta ttt tta gat att gtg ggt ttt gat aaa gag caa ttg caa<br>Gln Thr Leu Phe Leu Asp Ile Val Gly Phe Asp Lys Glu Gln Leu Gln<br>                330                     335                 340 | 1421 |
| caa caa tat tca caa tcc cca cta cca aac ttt att ttt acc ggc aca<br>Gln Gln Tyr Ser Gln Ser Pro Leu Pro Asn Phe Ile Phe Thr Gly Thr<br>             345                     350                 355 | 1469 |
| aca act tgg gct ggg ggg gaa acg aaa gag tat tat gct cag caa caa<br>Thr Thr Trp Ala Gly Gly Glu Thr Lys Glu Tyr Tyr Ala Gln Gln Gln<br>360                           365                     370 | 1517 |

```
gta aat gtg att aat aat gcg atc aat gaa act agc cct tat tat tta    1565
Val Asn Val Ile Asn Asn Ala Ile Asn Glu Thr Ser Pro Tyr Tyr Leu
375             380                 385                 390 ggt aaa gac tac gat cta ttt ttc aag ggg cat cct gct ggt ggc gtt    1613
Gly Lys Asp Tyr Asp Leu Phe Phe Lys Gly His Pro Ala Gly Gly Val
            395                 400                 405 att aac gac atc att ctt gga agc ttc cct gat atg atc aat att cca    1661
Ile Asn Asp Ile Ile Leu Gly Ser Phe Pro Asp Met Ile Asn Ile Pro
        410                 415                 420 gcc aag att tca ttt gag gtc ttg atg atg acg gat atg ttg cct gat    1709
Ala Lys Ile Ser Phe Glu Val Leu Met Met Thr Asp Met Leu Pro Asp
    425                 430                 435 aca gta gct ggt att gcg agc tct ctg tac ttc aca att cct gcc gat    1757
Thr Val Ala Gly Ile Ala Ser Ser Leu Tyr Phe Thr Ile Pro Ala Asp
440                 445                 450 aaa gtt aat ttt att gta ttt act tca tct gac act att act gat cgt    1805
Lys Val Asn Phe Ile Val Phe Thr Ser Ser Asp Thr Ile Thr Asp Arg
455                 460                 465                 470 gaa gag gct ctt aaa tca cca tta gta caa gtg atg cta acg ttg ggt    1853
Glu Glu Ala Leu Lys Ser Pro Leu Val Gln Val Met Leu Thr Leu Gly
            475                 480                 485 att gtt aaa gaa aaa gat gtt ctg ttc tgg gct gat cat aaa gta aac    1901
Ile Val Lys Glu Lys Asp Val Leu Phe Trp Ala Asp His Lys Val Asn
        490                 495                 500 tcg atg gaa gtt gcc att gat gaa gcc tgt act cgg atc att gca aag    1949
Ser Met Glu Val Ala Ile Asp Glu Ala Cys Thr Arg Ile Ile Ala Lys
    505                 510                 515 cga caa cca acc gcg agt gat tta cgc ttg gtt att gct att atc aaa    1997
Arg Gln Pro Thr Ala Ser Asp Leu Arg Leu Val Ile Ala Ile Ile Lys
520                 525                 530 aca att act gat ctt gag cgt att ggc gat gtg gca gaa agt att gct    2045
Thr Ile Thr Asp Leu Glu Arg Ile Gly Asp Val Ala Glu Ser Ile Ala
535                 540                 545                 550 aaa gtc gca tta gag agc ttt agt aat aag caa tat aac cta ttg gtt    2093
Lys Val Ala Leu Glu Ser Phe Ser Asn Lys Gln Tyr Asn Leu Leu Val
            555                 560                 565 tct tta gaa tct ctt ggc cag cat acg gtt cga atg ctg cat gag gtg    2141
Ser Leu Glu Ser Leu Gly Gln His Thr Val Arg Met Leu His Glu Val
        570                 575                 580 tta gat gcg ttt gct cgt atg gat gtt aaa gcc gca ata gaa gtg tac    2189
Leu Asp Ala Phe Ala Arg Met Asp Val Lys Ala Ala Ile Glu Val Tyr
    585                 590                 595 caa gaa gat gat cga att gat caa gag tat gag tcg ata gtc aga cag    2237
Gln Glu Asp Asp Arg Ile Asp Gln Glu Tyr Glu Ser Ile Val Arg Gln
600                 605                 610 cta atg gcc cat atg atg gaa gat cca agc tca att cct aat gta atg    2285
Leu Met Ala His Met Met Glu Asp Pro Ser Ser Ile Pro Asn Val Met
615                 620                 625                 630 aaa gtg atg tgg gcg gca cgt tct att gag cga gtg ggt gat cgc tgt    2333
Lys Val Met Trp Ala Ala Arg Ser Ile Glu Arg Val Gly Asp Arg Cys
            635                 640                 645 caa aac att tgt gag tac att atc tac ttt gtg aag ggt aaa gac gtt    2381
Gln Asn Ile Cys Glu Tyr Ile Ile Tyr Phe Val Lys Gly Lys Asp Val
        650                 655                 660 cgc cat acc aaa cca gat gat ttt ggt act atg ctc gat taatctatac    2430
Arg His Thr Lys Pro Asp Asp Phe Gly Thr Met Leu Asp
    665                 670                 675 aagaaacaag aaacaagaag gtcgccagca tcgtaaatgt ggcgaccttt tttaatgcaa  2490
```

```
aaaagcccctt ctaaaggtaa acgaagggcg agagtaacca aatggtcaaa attgagtgga      2550
tataacattc atgctgattt tgttattgtt gctatatttc aattagttaa ctgcgtttca      2610
gttaaagctg tattgtaaac cgacaccgcc tgcgacttct gatgacgagt atttaccgct      2670
cgtttcgtaa tggaaagttc ctgatacact taagttttcg ttgattccat aagcaccacc      2730
aaggctaaag ctt                                                        2743
```

<210> SEQ ID NO 3
<211> LENGTH: 38
<212> TYPE: DNA
<213> ORGANISM: Artificial Sequence
<220> FEATURE:
<223> OTHER INFORMATION: Any N = Inosine
<220> FEATURE:
<223> OTHER INFORMATION: Description of Artificial Sequence:synthethic
      probe

<400> SEQUENCE: 3

```
gcnaantann tngcnggnac nnnnccngan gcnccnaa                                38
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence:synthethic
      primer

<400> SEQUENCE: 4

```
gggggggaaa cgaaagagta ttatg                                             25
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence:synthethic
      primer

<400> SEQUENCE: 5

```
atttttcaag gggcatcctg ctgg                                              24
```

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:synthethic
      probe

<400> SEQUENCE: 6

```
aagatttcat ttgaggt                                                      17
```

<210> SEQ ID NO 7
<211> LENGTH: 10
<212> TYPE: DNA
<213> ORGANISM: HindIII linker (Takara Brewery, 4670A)

<400> SEQUENCE: 7

```
ccaagcttgg                                                              10
```

<210> SEQ ID NO 8
<211> LENGTH: 8
<212> TYPE: DNA
<213> ORGANISM: HindIII linker (Takara Brewery, 4693A)

<400> SEQUENCE: 8 ctctagag                                                                 8

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence:synthetic
      oligonucleotide

<400> SEQUENCE: 9
ttatgtgaat tcgcttaata tg                                                22

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence:synthetic
      oligonucleotide-Primer BST02

<400> SEQUENCE: 10
tttttatgtg aatgtggaat tcatgaagaa aatactga                               38

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence:synthetic
      oligonucleotide-Primer BST03

<400> SEQUENCE: 11
caaaacaatt actgattaat agtgaattgg cgatgtggca g                           41

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence:synthetic
      oligonucleotide-Primer BST04

<400> SEQUENCE: 12
tgttctgttc tgggcttagt gataagatct ctcgatggaa gttgcc                      46

<210> SEQ ID NO 13
<211> LENGTH: 19
<212> TYPE: PRT
<213> ORGANISM: Photobacterium damsela

<400> SEQUENCE: 13

Xaa Asn Ser Asp Asn Thr Ser Leu Lys Glu Thr Val Ser Ser Xaa Xaa
 1               5                  10                  15

Ala Xaa Val

<210> SEQ ID NO 14
<211> LENGTH: 9
<212> TYPE: PRT
<213> ORGANISM: Photobacterium damsela

<400> SEQUENCE: 14

Asp Tyr Leu Gly Ser Ser Ala Lys Lys

-continued

```
<210> SEQ ID NO 15
<211> LENGTH: 8
<212> TYPE: PRT
<213> ORGANISM: Photobacterium damsela

<400> SEQUENCE: 15

Phe Val Ser Trp Lys Ile Val Asn
 1               5

<210> SEQ ID NO 16
<211> LENGTH: 13
<212> TYPE: PRT
<213> ORGANISM: Photobacterium damsela

<400> SEQUENCE: 16

Ala Asn Tyr Leu Ala Gly Thr Ser Pro Asp Ala Pro Lys
 1               5                  10

<210> SEQ ID NO 17
<211> LENGTH: 16
<212> TYPE: PRT
<213> ORGANISM: Photobacterium damsela

<400> SEQUENCE: 17

Glu Thr Val Xaa Xaa Asn Ser Ala Val Val Val Glu Thr Glu Thr Tyr
 1               5                  10                  15

<210> SEQ ID NO 18
<211> LENGTH: 5
<212> TYPE: PRT
<213> ORGANISM: Photobacterium damsela

<400> SEQUENCE: 18

Tyr Asn Trp His Lys
 1               5

<210> SEQ ID NO 19
<211> LENGTH: 13
<212> TYPE: PRT
<213> ORGANISM: Photobacterium damsela

<400> SEQUENCE: 19

Gln Ala Ile Ser Phe Asp Phe Val Ala Pro Glu Leu Lys
 1               5                  10

<210> SEQ ID NO 20
<211> LENGTH: 9
<212> TYPE: PRT
<213> ORGANISM: Photobacterium damsela

<400> SEQUENCE: 20

Gln Leu Ile His Ile Ile Gln Ala Lys
 1               5

<210> SEQ ID NO 21
<211> LENGTH: 23
<212> TYPE: DNA
<213> ORGANISM: Unknown
<220> FEATURE:
<223> OTHER INFORMATION: Description of Unknown Organism:primer

<400> SEQUENCE: 21
cctggatgat ccggaagcta tcc                                         23
```

```
<210> SEQ ID NO 22
<211> LENGTH: 20
<212> TYPE: DNA
<213> ORGANISM: Unknown
<220> FEATURE:
<223> OTHER INFORMATION: Description of Unknown Organism:primer

<400> SEQUENCE: 22
tgacaccggg atccgcacga                                                     20

<210> SEQ ID NO 23
<211> LENGTH: 22
<212> TYPE: DNA
<213> ORGANISM: Unknown
<220> FEATURE:
<223> OTHER INFORMATION: Description of Unknown Organism:primer

<400> SEQUENCE: 23
tagttgcgta gatctcttcg cc                                                  22

<210> SEQ ID NO 24
<211> LENGTH: 19
<212> TYPE: DNA
<213> ORGANISM: Unknown
<220> FEATURE:
<223> OTHER INFORMATION: Description of Unknown Organism:primer

<400> SEQUENCE: 24
agttcggcgg acgggcccg                                                      19

<210> SEQ ID NO 25
<211> LENGTH: 21
<212> TYPE: DNA
<213> ORGANISM: Unknown
<220> FEATURE:
<223> OTHER INFORMATION: Description of Unknown Organism:primer

<400> SEQUENCE: 25
acggccacgg gacccatgtg g                                                   21

<210> SEQ ID NO 26
<211> LENGTH: 10
<212> TYPE: DNA
<213> ORGANISM: Unknown
<220> FEATURE:
<223> OTHER INFORMATION: Description of Unknown Organism:pAQNDeltaXH

<400> SEQUENCE: 26
tctagagctt                                                                10
```